United States Patent
Varga et al.

(10) Patent No.: US 11,906,097 B2
(45) Date of Patent: Feb. 20, 2024

(54) VENTILATION LEAK COMPONENT

(71) Applicant: Vyaire Medical, Inc., Mettawa, IL (US)

(72) Inventors: Christopher M. Varga, Laguna Hills, CA (US); Dennis White, Yorba Linda, CA (US); Thomas Dillingham, Aliso Viejo, CA (US)

(73) Assignee: Vyaire Medical, Inc., Mettawa, IL (US)

( * ) Notice: Subject to any disclaimer, the term of this patent is extended or adjusted under 35 U.S.C. 154(b) by 1181 days.

(21) Appl. No.: 16/560,882

(22) Filed: Sep. 4, 2019

(65) Prior Publication Data

US 2021/0060281 A1 Mar. 4, 2021

(51) Int. Cl.
*A61M 16/08* (2006.01)
*F16L 55/027* (2006.01)

(52) U.S. Cl.
CPC ... *F16L 55/02781* (2013.01); *A61M 16/0825* (2014.02); *F16L 55/02736* (2013.01); *A61M 2205/42* (2013.01)

(58) Field of Classification Search
CPC ............ A61B 5/0876; A61M 16/0003; A61M 16/0057; A61M 16/0069; A61M 16/024; A61M 16/06; A61M 16/0616; A61M 16/0622; A61M 16/0633; A61M 16/0666; A61M 16/0683; A61M 16/08; A61M 16/0816; A61M 16/0825; A61M 16/0866; A61M 16/0875; A61M 16/1065; A61M 16/109; A61M 16/16; A61M 16/208; A61M 2016/0042; A61M 2202/0085;

(Continued)

(56) References Cited

U.S. PATENT DOCUMENTS 3,586,021 A * 6/1971 McGuinness ......... A61M 16/00
128/204.24
3,714,944 A * 2/1973 Price .................... A61M 16/16
137/889

(Continued)

FOREIGN PATENT DOCUMENTS

EP 1436034 A2 4/2003
EP 1438086 A2 7/2004

(Continued)

OTHER PUBLICATIONS

Written Opinion of the International Preliminary Examining Authority for Application No. PCT/US2020/049065, dated Sep. 9, 2021, 8 pages.

(Continued)

*Primary Examiner* — Annette Dixon
(74) *Attorney, Agent, or Firm* — Morgan, Lewis & Bockius LLP

(57) ABSTRACT

Leakage components are described herein. The leakage component includes a first tubing housing and a plurality of leakage ports. The first tubular housing defines a first flow path between a first end portion and a second end portion. The plurality of leakage ports are formed in the first housing and in fluid communication with the first flow path. The fluid flow through the plurality of leakage ports is configured to entrain ambient air into the fluid flow exiting the plurality of leakage ports to decelerate the fluid flow.

20 Claims, 15 Drawing Sheets

(58) Field of Classification Search
CPC .. A61M 2202/0225; A61M 2205/0216; A61M 2205/332; A61M 2205/42; A61M 2205/75; A61M 2210/0618; A62B 7/12; F24F 13/26; G01F 1/28
See application file for complete search history.

(56) References Cited

U.S. PATENT DOCUMENTS

| | | | |
|---|---|---|---|
| 3,794,072 A * | 2/1974 | Diedrich | A61M 16/12 137/893 |
| 3,850,171 A * | 11/1974 | Ball | A61M 16/06 128/204.25 |
| 3,906,996 A * | 9/1975 | DePass | A61M 16/12 137/893 |
| 3,913,607 A * | 10/1975 | Price | A61M 16/127 431/114 |
| 3,977,432 A * | 8/1976 | Vidal | A61M 16/06 137/893 |
| 5,690,097 A * | 11/1997 | Howard | A61M 16/127 128/204.25 |
| 5,697,361 A * | 12/1997 | Smith | A62B 7/12 128/204.15 |
| 6,112,745 A | 9/2000 | Lang | |
| 6,152,129 A * | 11/2000 | Berthon-Jones | A61M 16/0057 128/204.23 |
| 6,615,830 B1 | 9/2003 | Serowski et al. | |
| 6,615,831 B1 * | 9/2003 | Tuitt | A61M 16/0069 128/204.22 |
| 6,679,265 B2 | 1/2004 | Strickland et al. | |
| 6,851,425 B2 | 2/2005 | Jaffre et al. | |
| 7,047,974 B2 | 5/2006 | Strickland et al. | |
| 7,059,328 B2 | 6/2006 | Wood | |
| 7,107,991 B2 | 9/2006 | Kolobow | |
| 7,174,919 B2 | 2/2007 | Kenyon et al. | |
| 7,278,423 B2 | 10/2007 | Serowski et al. | |
| 7,559,327 B2 | 7/2009 | Hernandez | |
| 7,568,482 B2 | 8/2009 | Jaffre et al. | |
| RE42,843 E | 10/2011 | Strickland et al. | |
| 8,113,313 B2 | 2/2012 | Lynch | |
| 8,181,649 B2 | 5/2012 | Brunner | |
| 8,353,293 B1 | 1/2013 | Fuhrman | |
| 8,397,727 B2 | 3/2013 | Ng et al. | |
| 8,439,035 B2 * | 5/2013 | Dantanarayana | A61B 5/0876 128/205.24 |
| 8,443,807 B2 | 5/2013 | McAuley et al. | |
| 8,479,741 B2 | 7/2013 | McAuley et al. | |
| 8,783,257 B2 | 7/2014 | McAuley et al. | |
| 9,095,673 B2 | 8/2015 | Barlow et al. | |
| 9,155,855 B2 | 10/2015 | Tebbutt et al. | |
| 9,174,018 B2 | 11/2015 | Ho et al. | |
| 9,228,542 B2 | 1/2016 | Anderson | |
| 9,242,061 B2 | 1/2016 | Lockhart et al. | |
| 9,339,622 B2 | 5/2016 | McAuley et al. | |
| 9,387,300 B2 | 7/2016 | Collazo et al. | |
| 9,539,405 B2 * | 1/2017 | McAuley | A61M 16/0825 |
| 9,687,626 B2 | 6/2017 | Amirav et al. | |
| 9,802,021 B2 | 10/2017 | Tebbutt et al. | |
| 9,844,640 B2 | 12/2017 | Darkin et al. | |
| 9,974,914 B2 * | 5/2018 | McAuley | A61M 16/0616 |
| 10,118,009 B2 | 11/2018 | Darkin et al. | |
| 10,576,240 B2 * | 3/2020 | Truschel | A61M 16/201 |
| 2005/0284482 A1 | 12/2005 | Patel | |
| 2007/0144522 A1 * | 6/2007 | Eger | A61M 16/205 128/204.26 |
| 2011/0146685 A1 | 6/2011 | Allan et al. | |
| 2011/0196251 A1 * | 8/2011 | Jourdain | A61M 16/0069 128/204.21 |
| 2013/0160769 A1 | 6/2013 | Ng et al. | |
| 2014/0283831 A1 * | 9/2014 | Foote | A61B 5/4812 128/204.19 |
| 2015/0297853 A1 | 10/2015 | Ho et al. | |
| 2016/0008558 A1 * | 1/2016 | Huddart | A61M 16/0683 128/205.25 |
| 2016/0287831 A1 | 10/2016 | Tebbutt et al. | |
| 2016/0317776 A1 | 11/2016 | Collazo et al. | |
| 2017/0021121 A1 | 1/2017 | Guney et al. | |
| 2017/0049982 A1 | 2/2017 | Kavermann et al. | |
| 2017/0197055 A1 | 7/2017 | Moody et al. | |
| 2018/0207389 A1 | 7/2018 | Fyfe et al. | |

FOREIGN PATENT DOCUMENTS

| | | |
|---|---|---|
| EP | 2376166 A2 | 6/2010 |
| EP | 3166674 A1 | 1/2016 |
| EP | 2263635 B1 | 4/2016 |
| EP | 1575650 B1 | 5/2016 |
| EP | 2629823 B1 | 12/2016 |
| EP | 3325071 A1 | 1/2017 |
| EP | 3135332 A1 | 3/2017 |
| EP | 2452716 B1 | 6/2017 |
| EP | 2429623 B1 | 7/2017 |
| EP | 2958613 B1 | 3/2018 |
| EP | 3372268 A1 | 9/2018 |
| EP | 1960025 B1 | 12/2018 |
| WO | WO-2009136333 A1 | 11/2009 |
| WO | WO-2015048849 A1 | 4/2015 |
| WO | WO-2018020466 A1 | 2/2018 |
| WO | WO-2018126863 A1 | 7/2018 |

OTHER PUBLICATIONS

International Preliminary Report on Patentability from the International Preliminary Examining Authority for Application No. PCT/US2020/049065, dated Dec. 22, 2021, 26 pages.
International Search Report and Written Opinion for Application No. PCT/US2020/049065, dated Dec. 7, 2020, 19 pages.

* cited by examiner

VENTILATION LEAK COMPONENT

FIELD OF THE INVENTION

The present disclosure generally relates to patient respiratory ventilation, and, in particular, to leakage components with leakage ports.

BACKGROUND

The delivery of a gas to patients, such as the delivery of air or oxygen in supplemental gas therapy, is a well-known treatment for a number of illnesses and conditions. For patients with respiratory difficulties, oxygen may be provided from a ventilator through a breathing circuit to a ventilation mask. The breathing circuit may include a leak port within the breathing circuit to allow exhaled gases during the expiratory phase to be cleared from the breathing circuit, permitting the patient to exhale with low effort and preventing the patient from rebreathing carbon dioxide from exhaled gases.

In some applications, flow through the leak port may not be effectively controlled.

SUMMARY

The disclosed subject matter relates to leakage components with leakage ports. In certain embodiments, a leakage component is disclosed that comprises a first tubular housing defining a first flow path between a first end portion and a second end portion; and a plurality of leakage ports formed in the first housing and in fluid communication with the first flow path, wherein fluid flow through the plurality of leakage ports is configured to entrain ambient air into the fluid flow exiting the plurality of leakage ports to decelerate the fluid flow.

In certain embodiments, a leakage component is disclosed that comprises a tubular first housing defining a first flow path between a first end portion and a second end portion; a ball joint surface adjacent to the second end portion and defined along an outer surface of the first housing; a plurality of leakage ports formed in the first housing and in fluid communication with the first flow path, wherein fluid flow through the plurality of leakage ports is configured to entrain ambient air into the fluid flow exiting the plurality of leakage ports to decelerate the fluid flow; a tubular second housing defining a second flow path, wherein the second housing is coupled to the first housing to permit fluid communication between the first flow path and the second flow path; and a socket surface defined within an inner surface of the second housing, wherein the socket surface is configured to movably couple with the ball joint surface.

In certain embodiments, a method to direct fluid flow is disclosed that comprises providing a tubular housing configured to accommodate a bulk inspiration flow and a bulk expiration flow; leaking a portion of the bulk expiration flow into environment via a plurality of leakage ports formed in the tubular housing, wherein each leakage port of the plurality of leakage ports comprises a fluid diversion member extending into the tubular housing and enshrouding a portion of the leakage port; diverting a portion of the bulk inspiration flow away from the plurality of leakage ports via the fluid diversion member; and diverting a portion of the bulk expiration flow toward the plurality of leakage ports formed in the tubular housing via the fluid diversion member.

In certain embodiments, a leakage component is disclosed that comprises a tubular first housing defining a first flow path between a first end portion and a second end portion; a ball joint surface adjacent to the second end portion and defined along an outer surface of the first housing; a tubular second housing defining a second flow path, wherein the second housing is coupled to the first housing to permit fluid communication between the first flow path and the second flow path; a socket surface defined within an inner surface of the second housing, wherein the socket surface is configured to movably couple with the ball joint surface; and a leakage path defined between the second end portion of the first housing and the socket surface of the second housing, wherein the leakage path is in fluid communication with the first flow path.

In certain embodiments, a method to direct fluid flow is disclosed that comprises providing a tubular housing configured to accommodate a bulk expiration flow; diverting a portion of the bulk expiration flow to a plurality of leakage ports formed in the tubular housing; and entraining ambient air into the portion of the bulk expiration flow leaking through the plurality of leakage ports to reduce a velocity of the portion of the bulk expiration flow leaking through the plurality of leakage ports.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
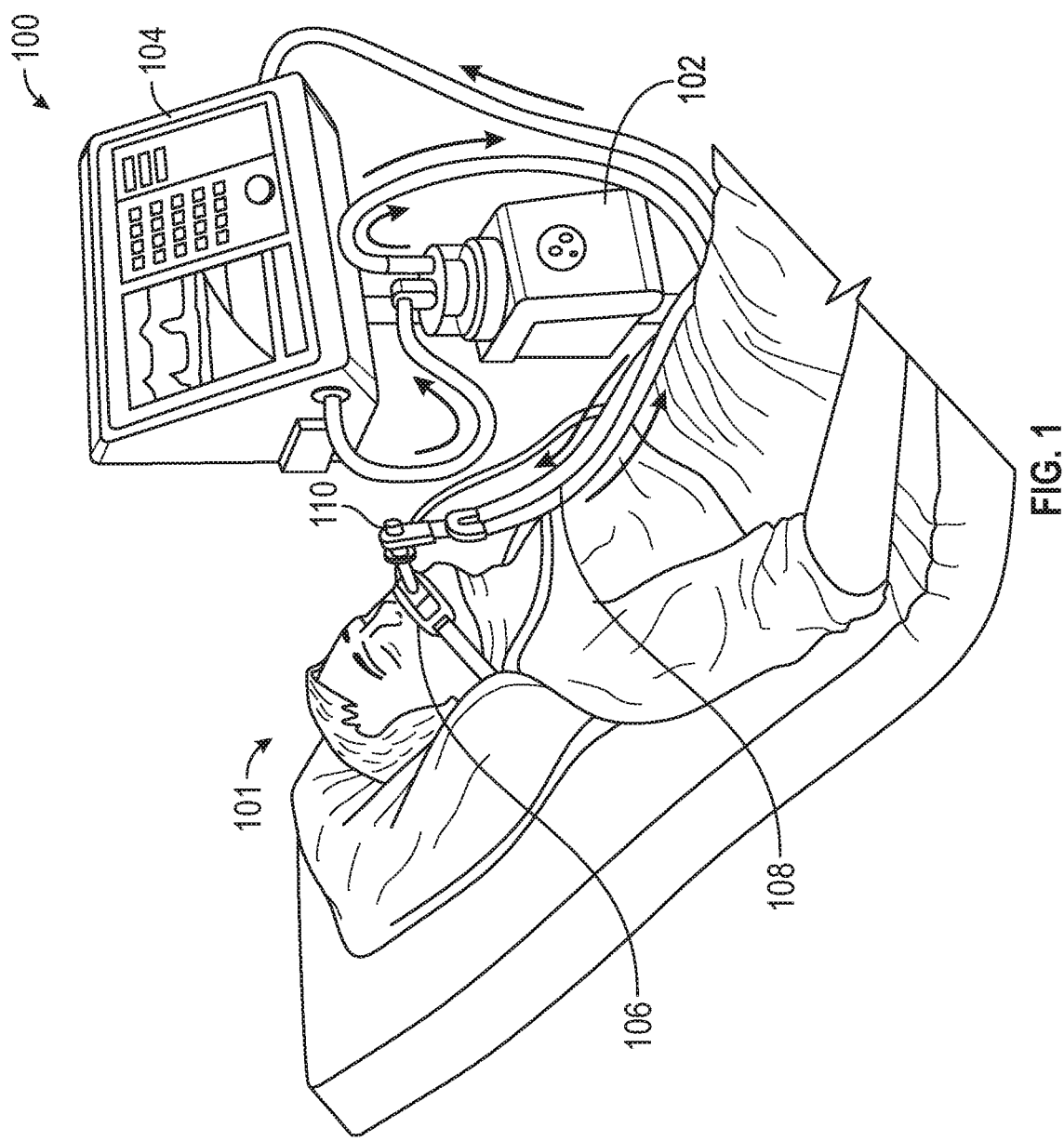
FIG. 1 is an illustration of a ventilation system, in accordance with various aspects of the present disclosure.

The disclosed leakage component incorporates features to permit and control the flow of exhaled gases during the expiratory phase. The leakage component can utilize fluid dynamics to reduce noise during operation and reduce leakage of supplemental gas flow during an inspiratory phase. Further, the leakage component can allow for improved adjustability.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of supplemental gas to a patient by a medical practitioner using the disclosed leakage component, it is to be understood that this description is only an example of usage and does not limit the scope of the claims. Various aspects of the disclosed leakage component may be used in any application where it is desirable to control the flow of fluids such as inhaled and/or exhaled gases.

The disclosed leakage component overcomes several challenges discovered with respect to certain leakage components. One challenge with certain conventional leakage components is that during the inspiratory cycle, certain conventional leakage components may leak or direct supplemental gas flow to the environment instead of the patient, wasting air, oxygen, or other gases directed toward the patient, causing the ventilator to deliver higher average and peak flow rates to reach the targeted volume and pressure of gas flow desired to reach the patient. Further, because of the higher flow rates, humidification of the supplemental gas flow may be a challenge, resulting in water splashing and/or spitting during the delivery of supplemental gases. Because certain conventional leakage components may require high flow rates to deliver a desired amount of gas flow, the use of conventional leakage components is undesirable. Another challenge with certain conventional leakage components is that valves used in certain conventional leakage components may be expensive and prone to failure. Because failure of valves within certain conventional leakage components may pose safety issues, the use of conventional leakage components is undesirable. Another challenge with certain conventional leakage components is that certain conventional leakage components may be noisy during operation. Because noisy operation may be unsuitable for care environments and bothersome to patients and/or caregivers, the use of conventional leakage components is undesirable. Another challenge with certain conventional leakage components is that certain conventional leakage components may lack adjustability. Because certain conventional leakage components may not provide sufficient range of motion to suitably adjust the breathing circuit, the use of conventional leakage components is undesirable.

Therefore, in accordance with the present disclosure, it is advantageous to provide a valve-less leakage component as described herein that allows for exhaled gases during the expiratory phase to be cleared from the breathing circuit, while preventing excess leaking of gas flow into the environment during the inspiratory phase. Further, it is advantageous to provide a leakage component that reduces noise during operation. The disclosed leakage component provides a plurality of leakage ports to entrain ambient air into the fluid flow exiting the leakage component. Further, it is advantageous to provide a leakage component that allows for adjustability to accommodate a breathing circuit and/or the position of the patient. The disclosed leakage component can provide an adjustable coupling to allow a range of motion for the leakage component.

Examples of leakage components that allow for exhaled gases to be cleared from the breathing circuit while allowing for ambient air to be entrained during operation are now described.

FIG. 1 is an illustration of a ventilation system 100, in accordance with various aspects of the present disclosure. In the depicted example, the ventilation system 100 can assist a patient 101 with breathing. During operation, a ventilator 102 can deliver a supplemental gas flow, such as oxygen, to the patient 101 via a breathing circuit 108. As illustrated, a ventilation mask 106 can direct supplemental gas from the breathing circuit 108 to the mouth and/or nose of the patient 101. In some embodiments, a controller 104 can be used to permit a clinician to control the operation of the ventilator 102.

As described herein, the ventilation system 100 can include a leakage component 110 to allow for exhaled gases to be vented or leaked to the environment while allowing for supplemental gas flow from the ventilator 102. In some embodiments, the leakage component 110 is disposed between and couples the ventilation mask 106 to the breathing circuit 108. Optionally, and as described herein, the leakage component 110 can be movable or flexible to adjust the position of the tubing of the breathing circuit 108 relative to the ventilation mask 106.

In the depicted example, the leakage component 110 defines a gas flow path between the breathing circuit 108 and the ventilation mask 106, allowing for the flow of gases between the breathing circuit 108 and the patient 101. As described herein, the leakage component 110 defines a leakage path to allow for gases exhaled by the patient 101 during the expiratory phase to be cleared from the breathing circuit 108. Advantageously, the leakage component 110 can allow the patient 101 to exhale with lower effort while preventing the patient 101 from rebreathing exhaled carbon dioxide.

Figure 2A:
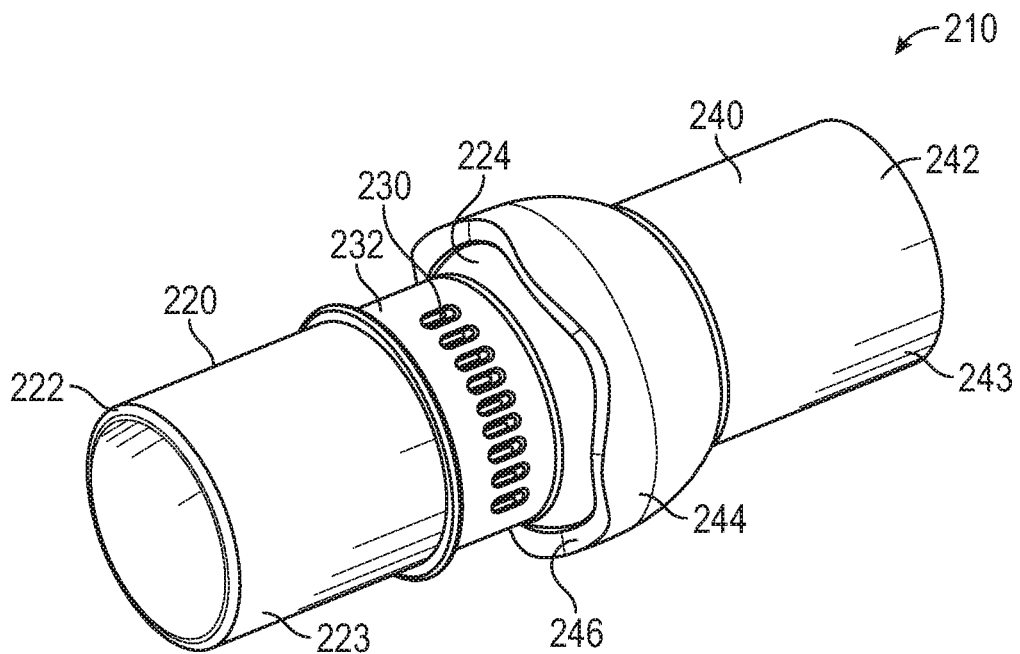
FIG. 2A is a perspective view of a leakage component, in accordance with various aspects of the present disclosure.
Figure 2B:
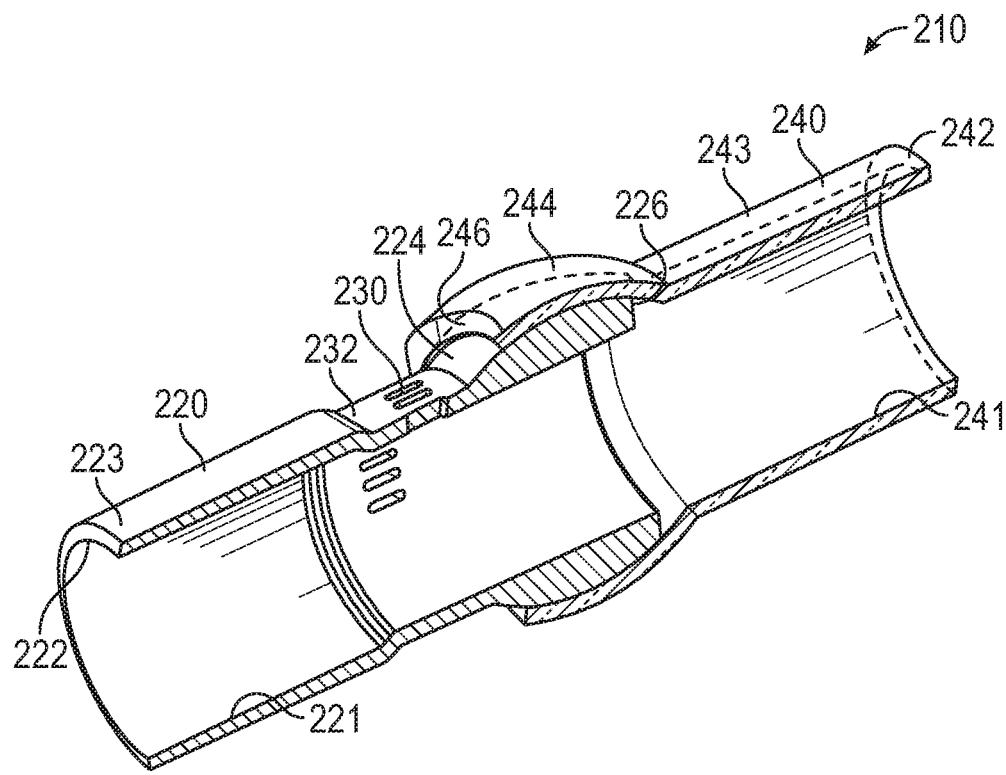
FIG. 2B is a cross-sectional view of the leakage component of FIG. 2A, in accordance with various aspects of the present disclosure.

FIG. 2A is a perspective view of a leakage component 210, in accordance with various aspects of the present disclosure. FIG. 2B is a cross-sectional view of the leakage component 210 of FIG. 2A, in accordance with various aspects of the present disclosure.

With reference to FIGS. 2A and 2B, the leakage component 210 controls and/or directs the flow of gasses between a patient, a ventilator, and the environment. In the depicted example, the leakage component 210 can be configured to be coupled to a breathing circuit at any point between a patient and a ventilator. For example, a ventilator-side tubular housing 220 can be coupled to a ventilator via a breathing circuit and a patient-side tubular housing 240 can be coupled to a ventilation mask. In some embodiments of the present disclosure, the tubular housing 220 can be coupled to a patient, such as through a ventilation mask, and the tubular housing 240 can be coupled to a ventilator, such as through a breathing circuit.

In some embodiments, tubing or a fitting from the breathing circuit can be positioned over the outer surface 223 of the ventilator-side tubular housing 220 to couple the breathing circuit to the leakage component 210 and to provide fluid communication between the breathing circuit and a ventilator-side opening 222. Optionally, tubing or fittings can be positioned within an inner surface 221 to couple the breathing circuit to the leakage component 210.

Similarly, in some embodiments, tubing or a fitting from the ventilation mask, or other breathing circuit component, can be positioned within the inner surface 241 of the patient-side tubular housing 240 to couple the breathing circuit component to the leakage component 210 and to provide fluid communication between the breathing circuit component and a patient-side opening 242. Optionally, tubing or fittings can be positioned over an outer surface 243 to couple the breathing circuit component to the leakage component 210.

As illustrated, the ventilator-side tubular housing 220 and the patient-side tubular housing 240 are coupled or connected to allow fluid communication or otherwise define a flow path between the ventilator-side opening 222 and the patient-side opening 242. In some embodiments, the ventilator-side tubular housing 220 and the patient-side tubular housing 240 are movably connected to allow the ventilator-side tubular housing 220 and/or the patient-side tubular housing 240 to move relative to each other, while allowing fluid communication therebetween.

In the depicted example, the leakage component 210 includes a ball and socket joint to allow the ventilator-side tubular housing 220 and the patient-side tubular housing 240 to move relative to each other. In some embodiments, the ventilator-side tubular housing 220 includes a ball joint surface 224 defined on the outer surface 223. As illustrated, the ball joint surface 224 can be disposed opposite to the ventilator-side opening 222. In the depicted example, the ball joint surface 224 can have a generally spherical or rounded shape and can define a ball joint edge 226 at an end portion of ventilator-side tubular housing 220 that is opposite to the ventilator-side opening 222.

In some embodiments, the patient-side tubular housing 240 includes a mating socket 244 configured to couple or engage with the ball joint surface 224 of the ventilator-side tubular housing 220. The socket 244 can be disposed opposite to the patient-side opening 242. The socket 244 can have a generally spherical or rounded shape complimentary or otherwise configured to receive the ball joint surface 224. The socket 244 can define a socket edge 246 at an end portion of the patient-side tubular housing 240 that is opposite to the patient-side opening 242.

As illustrated, a portion of the ventilator-side tubular housing 220 can be disposed within the patient-side tubular housing 240 to permit the ball joint surface 224 to mate or engage with the socket 244. In some embodiments, the ball joint surface 224 and/or the socket 244 can expand, contract, or otherwise deform to allow the ball joint surface 224 to be placed into engagement with the socket 244. As can be appreciated, by forming a ball joint, the ventilator-side tubular housing 220 can be moved relative to the patient-side tubular housing 240, permitting superior adjustment and flexibility. For example, by forming the ball joint, the ventilator-side tubular housing 220 and/or the patient-side tubular housing 240 can be moved relative to each other in any of a yaw, pitch, and/or roll direction. In some embodiments, the socket edge 246 of the socket 244 can be scalloped or undulating to permit a greater range of motion to the ventilator-side tubular housing 220 relative to the patient-side tubular housing 240.

Figure 2C:
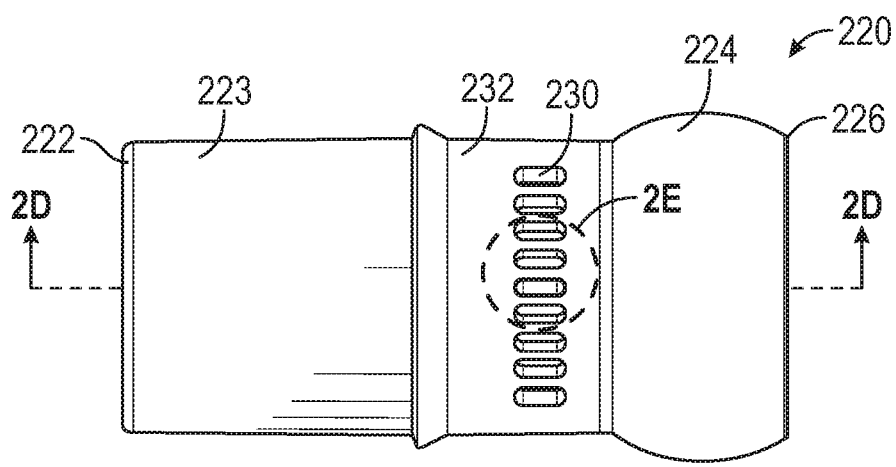
FIG. 2C is a top plan view of a ventilator-side tubular housing of the leakage component of FIG. 2A, in accordance with various aspects of the present disclosure.
Figure 2D:
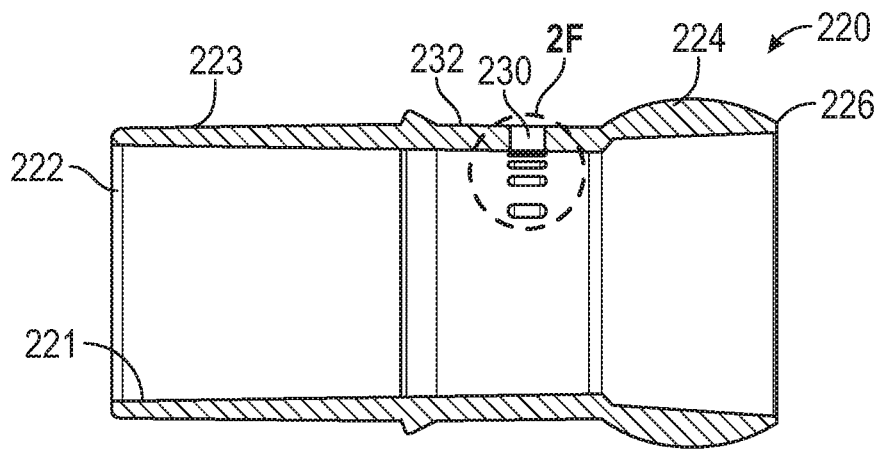
FIG. 2D is a cross-sectional view of the ventilator-side tubular housing of FIG. 2C taken along section line 2D-2D, in accordance with various aspects of the present disclosure.

FIG. 2C is a top plan view of a ventilator-side tubular housing 220 of the leakage component 210 of FIG. 2A, in accordance with various aspects of the present disclosure. FIG. 2D is a cross-sectional view of the ventilator-side tubular housing 220 of FIG. 2C taken along section line 2D-2D, in accordance with various aspects of the present disclosure. With reference to FIGS. 2A-2D, the ventilator-side tubular housing 220 can include one or more leakage ports 230 to direct and/or control the flow of gases through the leakage component 210.

In the depicted example, the leakage ports 230 can be formed to extend through the outer surface 223 to the inner surface 221 to be in fluid communication with the flow path defined by the ventilator-side tubular housing 220 and the leakage component 210 generally. In some embodiments, the leakage ports 230 can be disposed near the ball joint surface 224 of the ventilator-side tubular housing 220. Optionally, the leakage ports 230 can be disposed in a recessed area 232 of the outer surface 223.

As can be appreciated, the leakage component 210 can include any suitable number of leakage ports 230, including 1 port, 2 ports, 4 ports, 5 ports, 6 ports, 8 ports, 10 ports, 15 ports, 20 ports, etc. As illustrated, the leakage ports 230 can be positioned or arranged in a distributed pattern or array along the ventilator-side tubular housing 220. In some embodiments, the leakage ports 230 can be disposed in groups or patterns including groups of 2 ports, groups of 3 ports, groups of 5 ports, groups of 10 ports, etc. As can be appreciated, the groups of leakage ports 230 can vary in number.

In some embodiments, the leakage ports 230 can be disposed along a circumference of the ventilator-side tubular housing 220. Optionally, the leakage ports 230 can be disposed along a portion of the circumference of the ventilator-side tubular housing 220. For example, the leakage ports 230 can be disposed along 180 degrees of the circumference of the ventilator-side tubular housing 220. As can be appreciated, the leakage ports 230 can be disposed along approximately 170 degrees of the circumference, 150 degrees of the circumference, 120 degrees of the circumference, 90 degrees of the circumference, 60 degrees of the circumference, etc. Advantageously, by disposing the leakage ports 230 within 180 degrees of the circumference of the ventilator-side tubular housing 220, leakage flow can be directed as desired, such as away from the patient and/or care giver.

In some embodiments, the leakage ports 230 can be equidistantly spaced apart. Optionally, the leakage ports 230 can be disposed with varied spacing as well. For example, in some embodiments, the leakage ports 230 can be spaced apart or have a separation (or radial) distance 237 (as shown in FIG. 2E) from each other with a spacing including, but not limited to approximately 0.5 mm, 1.0 mm, 1.5 mm, 2.0 mm, 2.5 mm, 3.0 mm, or 3.5 mm.

Figures 2E, 2F:
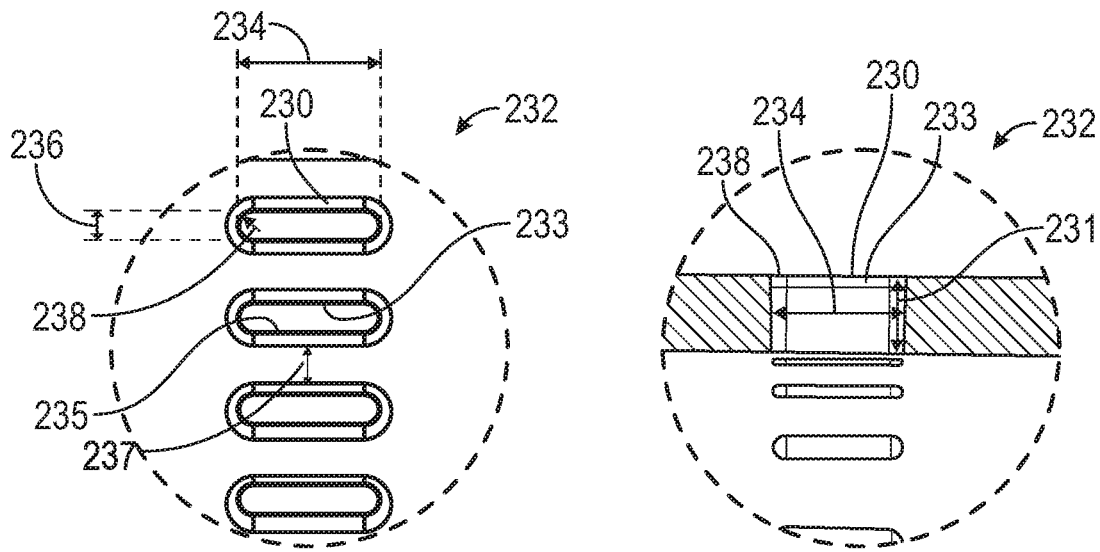
FIG. 2E is a detailed view of a recessed area of the ventilator-side tubing housing of FIG. 2C, in accordance with various aspects of the present disclosure.
FIG. 2F is a detail cross-sectional view of the recessed area of the ventilator-side tubular housing of FIG. 2D, in accordance with various aspects of the present disclosure.

FIG. 2E is a detailed view of a recessed area 232 of the ventilator-side tubular housing 220 of FIG. 2C, in accordance with various aspects of the present disclosure. FIG. 2F is a detailed cross-sectional view of the recessed area 232 of the ventilator-side tubular housing 220 of FIG. 2D, in accordance with various aspects of the present disclosure. With reference to FIGS. 2A-2F, the leakage ports 230 can be defined or otherwise designed to have a geometry that controls the flow of gases therethrough.

In some embodiments, the leakage ports 230 can be formed as slots that have an elongate profile with a port length 234 longer than a port width 236. Optionally, the port width 236 can be in a range between approximately 0.25 to approximately 5 mm, or can be approximately 0.25 mm, 0.5 mm, 0.75 mm, 1 mm, 2 mm, 4 mm, and/or 5 mm. The port length 234 can be in a range between approximately 0.75 mm to approximately 45 mm, or approximately 0.75 mm, 1.5 mm, 2.25 mm, 3 mm, 6 mm, 12 mm, and/or 45 mm. As can be appreciated, the port length 234 and/or the port width 236 can be selected to allow the leakage port 230 to have an aspect ratio between the port length 234 and the port width 236 ranging between 2:1 to 10:1, or an aspect ratio of approximately 3:1, 4:1, 5:1, 6:1, 7:1, 8:1, and/or 9:1. As illustrated, the leakage ports 230 can be elongated to extend along a flow axis of the ventilator-side tubular housing 220. Optionally, the leakage ports 230 can have any suitable geometric profile, including, but not limited to circular profiles, polygonal profiles, etc.

As illustrated, the leakage ports 230 can have a generally stadium or discorectangular profile or shape. In the depicted example, the leakage ports 230 can include an elongated rectangular shape with semi-circular ends 238. Optionally, the semi-circular ends 238 can have a diameter that is the same or similar to the port width 236.

In the depicted example, the leakage ports 230 include a port depth 231 that extends through the material of the ventilator-side tubular housing 220. As can be appreciated, the thickness of the ventilator-side tubular housing 220 can be modified to adjust the port depth 231 and alter the performance of the leakage ports 230. In some embodiments, the leakage ports 230 include port walls 233, 235.

The port walls 233, 235 can extend parallel to each other. For example, the port walls 233, 235 can extend in a direction that is parallel to each other in a direction along the flow axis or in a direction transverse to the flow axis. As can be appreciated, a distance between the port walls 233, 235 can taper toward or away from each other in any direction along the flow axis or transverse to the flow axis. In some embodiments, the port walls 233, 235 of a leakage port 230 can be parallel to the port walls 233, 235 of another leakage port 230. For example, the port walls 233, 235 of a leakage port 230 can extend in a direction that is parallel to the port walls 233, 235 of another leakage port 230. As can be appreciated, the port walls 233, 235 of a leakage port 230 can be parallel to the port walls 233, 235 of another leakage port 230, or a distance between the port walls 233, 235 of adjacent leakage ports 230 can taper toward or away from each other. In other words, in some embodiments, the port walls 233, 235 of the leakage ports 230 may be parallel to common plane. In some embodiments, planes parallel to the port walls 233, 235 may radially converge toward a direction of the flow axis.

Figure 2G:
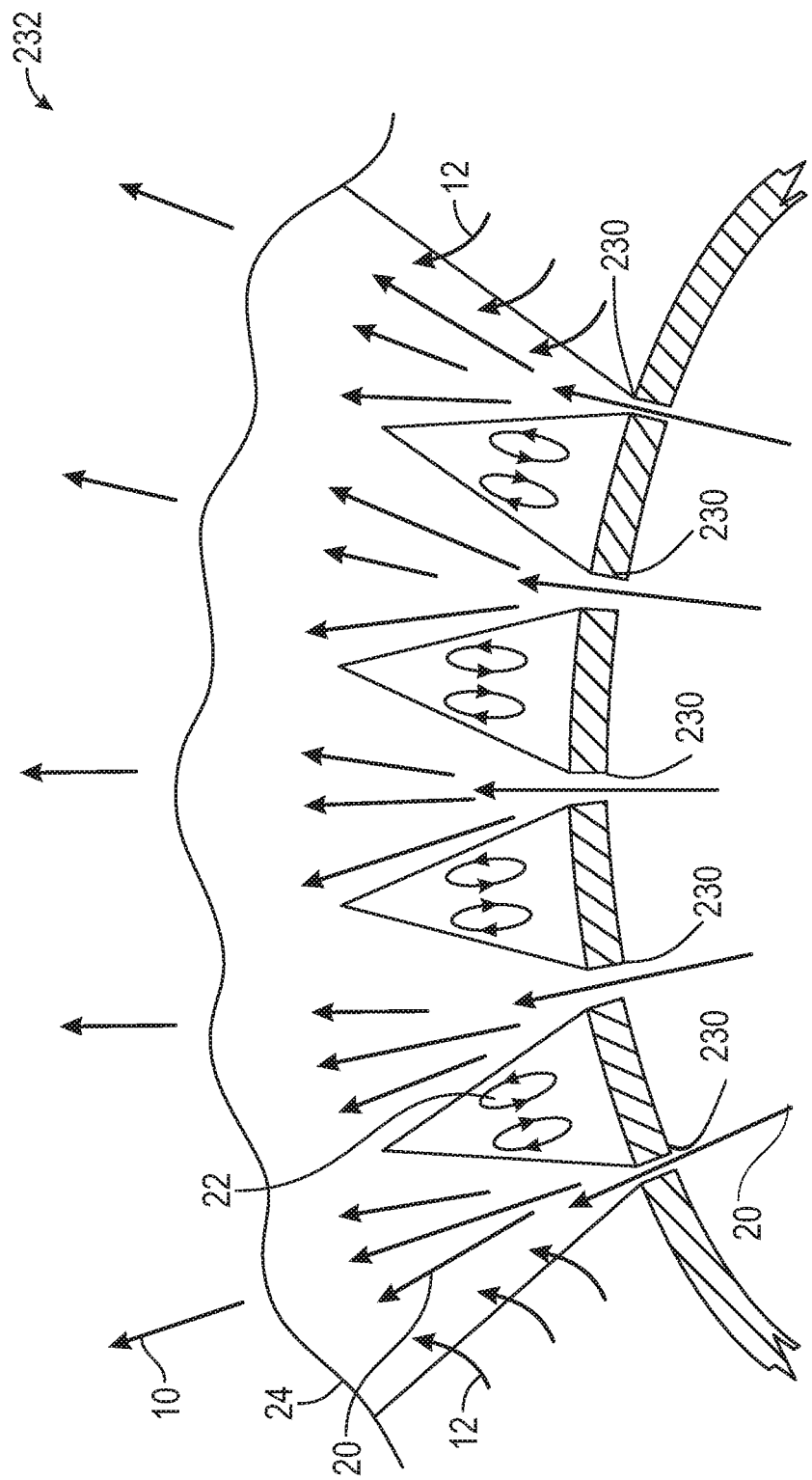
FIG. 2G is a detail cross-sectional view of the recessed area with an example leakage flow shown, in accordance with various aspects of the present disclosure.

FIG. 2G is a detailed cross-sectional view of a portion of the leakage component 210 comprising leakage ports 230 with an example leakage flow 20 shown, in accordance with various aspects of the present disclosure. As can be appreciated, the arrangement and geometry of the leakage ports 230 can control the fluid dynamics or the general behavior of the leakage flow 20 from the leakage component 210.

For example, the configuration of the leakage ports 230 can reduce the sound energy or level during operation for a given flow rate compared to certain conventional leakage devices. In some embodiments, the profile and arrangement (e.g. the shape, number, and proximity) of the leakage ports 230 can effect advantageously leakage flow dynamics and can cause leakage flow 20 from the leakage ports 230 to entrain surrounding ambient air 12 into the leakage flow 20, causing a reduction in the difference of velocity between the combined gas front 24 and the ambient air 10, and therefore, a reduction in sound energy.

In some applications, the shape of the leakage ports 230 (e.g. discorectangular shape) can provide a leakage ports 230 having a large perimeter relative to the surface area (or leakage area) of the leakage ports 230 (i.e. maximizing the perimeter for a given leakage area). For example, a leakage port with a discorectangular shape has a larger perimeter relative to a leakage port with a circular perimeter. As a result, the area of interaction between the leakage flow 20 and the surrounding fluid is increased, leading to increased mixing of entrained surrounding ambient air 12 with the leakage flow 20, and resulting in deceleration of the combined gas front 24.

In some applications, the separation of a leakage port 230 from a neighboring leakage port 230 (for example, a spacing of 1.9 mm or 2.9 times the diameter of the semi-circular end 238 of the leakage port 230 or other spacing configurations as described herein) can provide for the deceleration of the combined gas front 24 and therefore reduce sound energy. For example, due to the separation of the leakage ports 230, each of the leakage flows 20 exiting the respective leakage ports 230 can behave as confined jets, creating recirculation zones 22 between the confined jets. Advantageously, the recirculation zones 22 can reduce the momentum of the leakage flows 20 by entraining a portion of the leakage flows 20, reducing the velocity of the combined gas front 24. Further, in some applications, the separation or increased radial distance between the leakage ports 230 (shown as separation distance 237 in FIG. 2E) can create neighboring leakage flows 20 that undergo parallel planar jet-type "flapping" instability, increasing mixing and deceleration of the leakage flows 20, and in turn, reducing the velocity of the combined gas front 24. In some embodiments, leakage flow 20 from a first leakage port 230 can entrain the leakage flow 20 from another leakage port 230. Further, in some embodiments, leakage flow 20 from a first leakage port 230 can entrain the leakage flow 20 from neighboring leakage ports 230 disposed on either side of the first leakage port 230.

Advantageously, the configuration of leakage ports 230 described herein can significantly reduce sound levels during operation compared to certain conventional leakage devices. For example, embodiments of the leakage component described herein can provide a reduction of 4-5 dbA (approximately a 30%-40% perceived difference in loudness) at leakage rates above 40 liters per minute compared to certain conventional leakage devices.

Figure 3A:
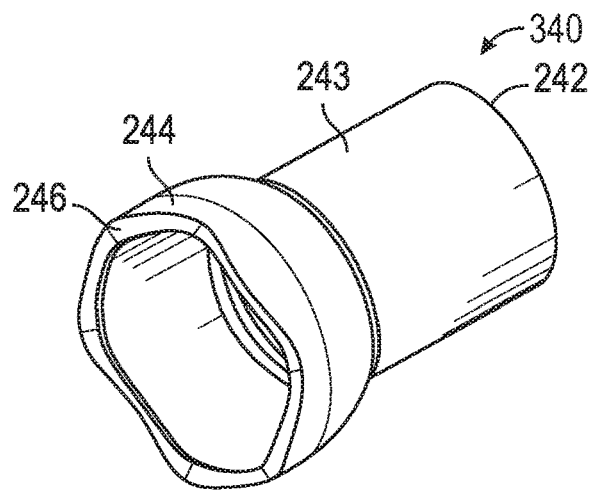
FIG. 3A is a perspective view of a patient-side tubular housing, in accordance with various aspects of the present disclosure.
Figure 3B:
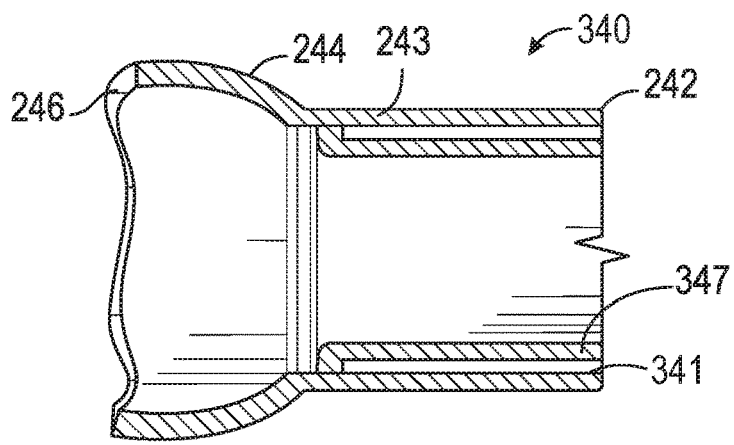
FIG. 3B is a cross-sectional view of the patient-side tubular housing, in accordance with various aspects of the present disclosure.

FIG. 3A is a perspective view of a patient-side tubular housing 340, in accordance with various aspects of the present disclosure. FIG. 3B is a cross-sectional view of the patient-side tubular housing 340, in accordance with various aspects of the present disclosure. With reference to FIGS. 3A and 3B, the patient-side tubular housing 340 includes features that are similar to the patient-side tubular housing 240, as previously described. Therefore, unless noted, similar features are identified by similar reference numerals. In the depicted example, the patient-side tubular housing 340 can include a tubing receptacle 347 disposed within the inner surface 341. The patient-side tubular housing 340 can receive tubing from the ventilation mask and/or other breathing circuit components in the cavity defined between the tubing receptacle 347 and the inner surface 341. Advantageously, the tubing receptacle 347 can retain tubing from the ventilation mask without disrupting airflow through the inner surface 341 of the patient-side tubular housing 340.

Figure 4A:
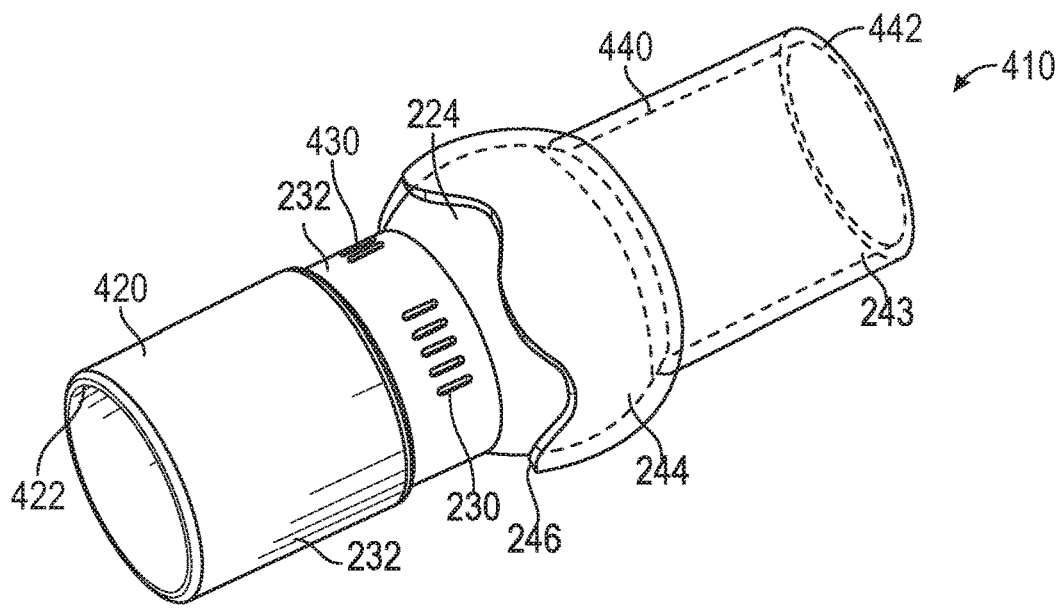
FIG. 4A is a perspective view of a leakage component with a patient-side tubular housing shown in broken lines, in accordance with various aspects of the present disclosure.
Figure 4B:
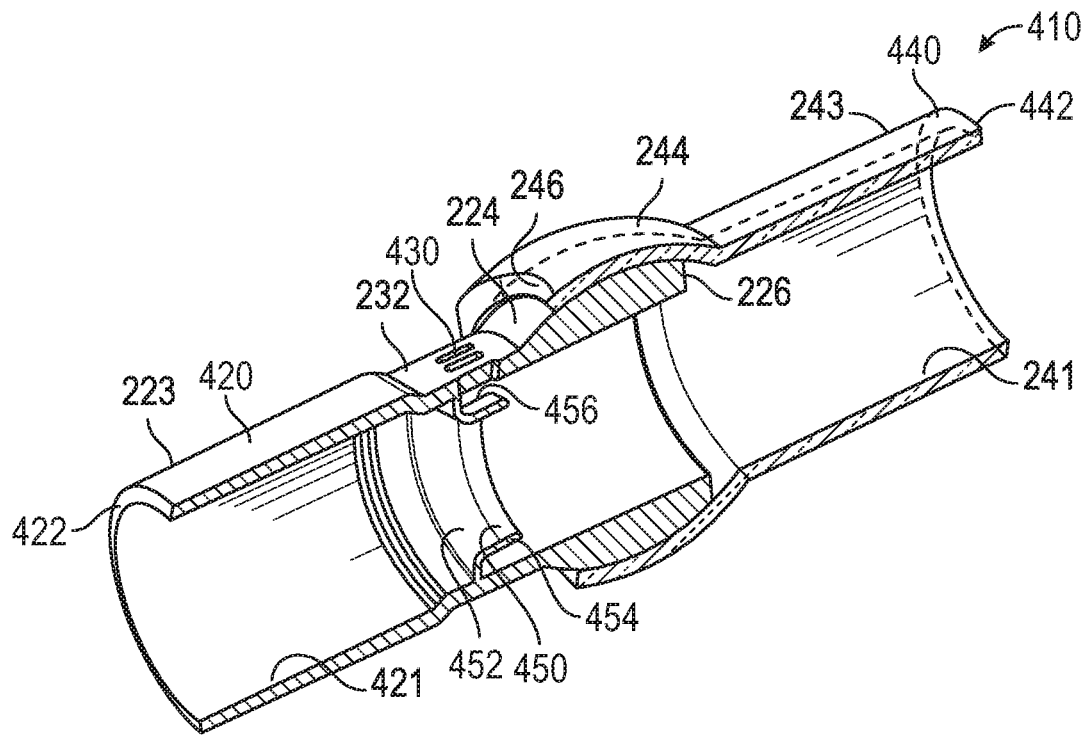
FIG. 4B is a cross-sectional perspective view of the leakage component of FIG. 4A, in accordance with various aspects of the present disclosure.
Figure 4C:
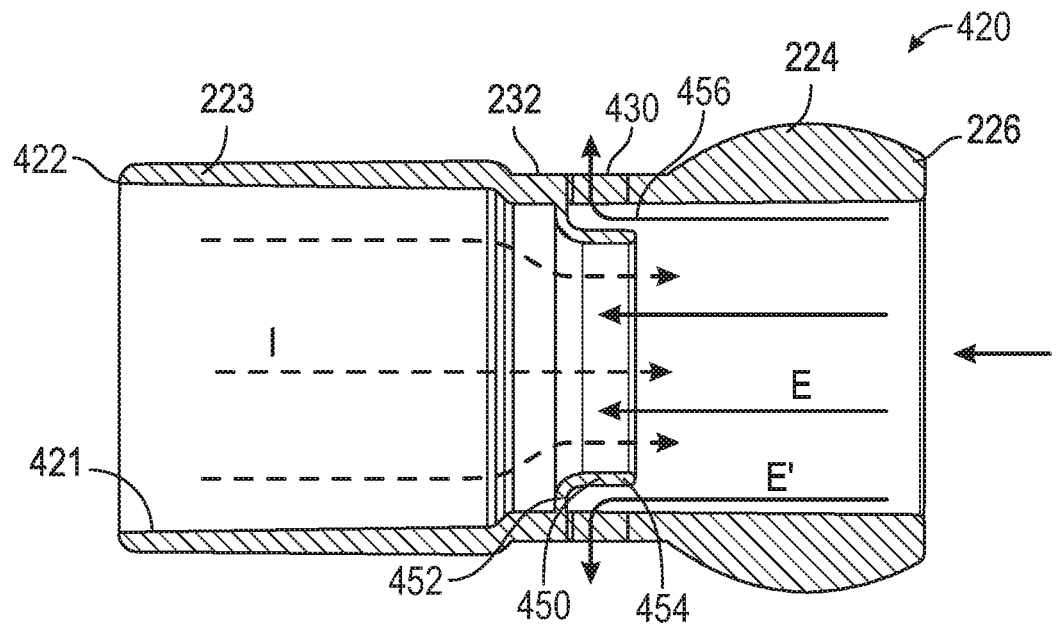
FIG. 4C is a cross-sectional elevation view of a ventilator-side tubular housing of FIG. 4A, in accordance with various aspects of the present disclosure.

FIG. 4A is a perspective view of a leakage component 410 with a patient-side tubular housing 440 shown in broken lines, in accordance with various aspects of the present disclosure. FIG. 4B is a cross-sectional perspective view of the leakage component 410 of FIG. 4A, in accordance with various aspects of the present disclosure. FIG. 4C is a cross-sectional elevation view of a ventilator-side tubular housing 420 of FIG. 4A, in accordance with various aspects of the present disclosure. The leakage component 410 includes features that are similar to the leakage component 210, as previously described. Therefore, unless noted, similar features are identified by similar reference numerals. With reference to FIGS. 4A-4C, the leakage component 410 includes a fluid diversion member 450 to direct expiratory flow (E) toward the leakage ports 430 during expiration and direct inspiratory flow (I) through the leakage component 410, at least partially bypassing the leakage ports 430 during inspiration.

In the depicted example, the fluid diversion member 450 is disposed within the inner surface 421 of the ventilator-side tubular housing 420. In some embodiments, the fluid diversion member 450 can be disposed adjacent to the leakage ports 430 to direct expiratory flow toward the leakage ports 430. Optionally, the leakage component 410 can include any suitable number of leakage ports 430, for example, ten leakage ports 430. As illustrated, the leakage ports 430 can be disposed in two groups.

As illustrated, a radial extension 452 of the fluid diversion member 450 extends radially from the inner surface 421 toward the center of the ventilator-side tubular housing 420. In some embodiments an axial extension 454 extends axially from the radial extension 452 to at least partially shroud the leakage ports 430. Optionally, the fluid diversion member 450 can be circumferentially disposed around the entire circumference of the ventilator-side tubular housing 420. In some embodiments, the fluid diversion member 450 can be circumferentially disposed around one or more portions of the circumference of the ventilator-side tubular housing 420. As illustrated, the geometry of the fluid diversion member 450 can define a fluid diversion cavity 456 between the inner surface 421 and the fluid diversion member 450.

During operation, the fluid diversion member 450 interacts with the flow through the leakage component 410. For example, during expiration, the geometry of the fluid diversion member 450 defines a flow path that guides a portion of the bulk expiratory flow toward the leakage ports 430. Advantageously, by directing a portion of the bulk expiratory flow (E') toward the leakage ports 430, the fluid diversion member 450 can allow for carbon dioxide to be cleared from the leakage component 410. Further, during inspiration, the geometry of the fluid diversion member 450 defines a flow path that guides bulk inspiratory flow from the ventilator-side opening 422 to the patient-side opening 442, bypassing or otherwise guiding bulk inspiratory flow away from the leakage ports 430. Advantageously, by directing bulk inspiratory flow away from the leakage ports 430, the fluid diversion member 450 can reduce the amount of supplemental gas flow that is lost, effectively reducing the amount of supplemental gas flow required to achieve a target therapeutic effect.

Figure 5:
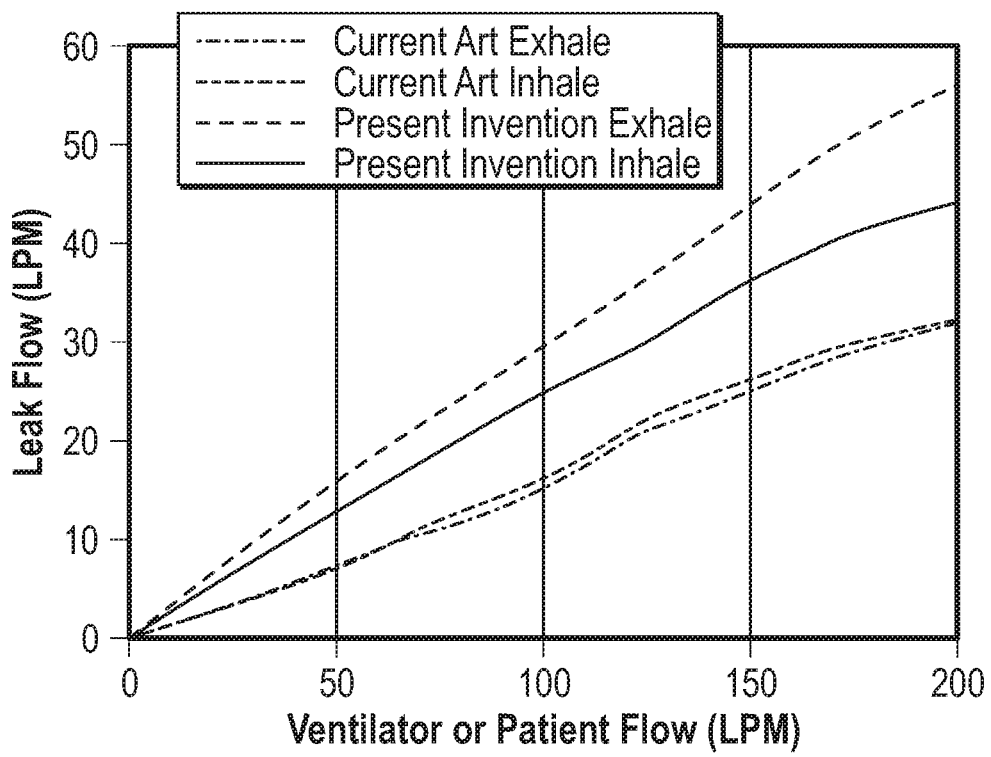
FIG. 5 is a chart depicting a leak flow rate compared to a ventilator or patient flow rate, in accordance with various aspects of the present disclosure.

FIG. 5 is a chart depicting a leak flow rate compared to a ventilator or patient flow rate, in accordance with various aspects of the present disclosure. As illustrated in FIG. 5, compared to certain conventional leakage devices, which demonstrate similar leakage rates during inhalation and exhalation, the fluid diversion member 450 allows for the leakage component 410 to have a different leakage rate through the leakage ports 430 depending on the direction of the bulk fluid flow. As illustrated, the leakage component 410 can provide for a 20% or more difference in leakage rate between the inspiration expiration. In other words, the leakage component 410 can provide 20% or more leakage in the exhalation direction compared to the inhalation direction.

Figure 6A:
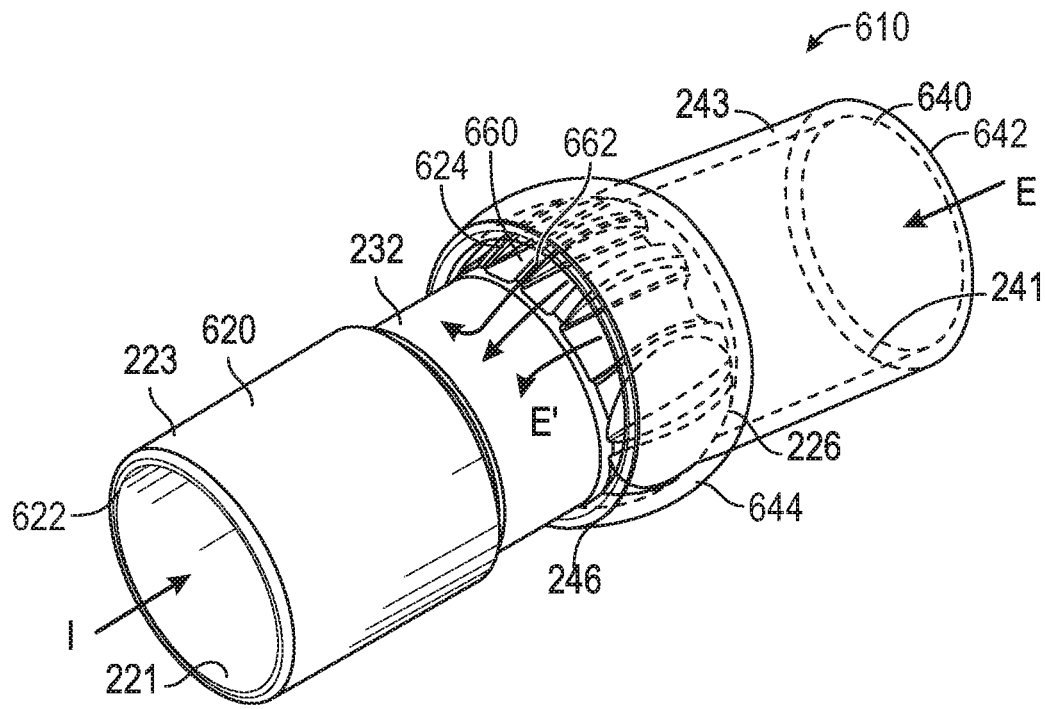
FIG. 6A is a perspective view of a leakage component with a patient-side tubular housing shown in broken lines, in accordance with various aspects of the present disclosure.
Figure 6B:
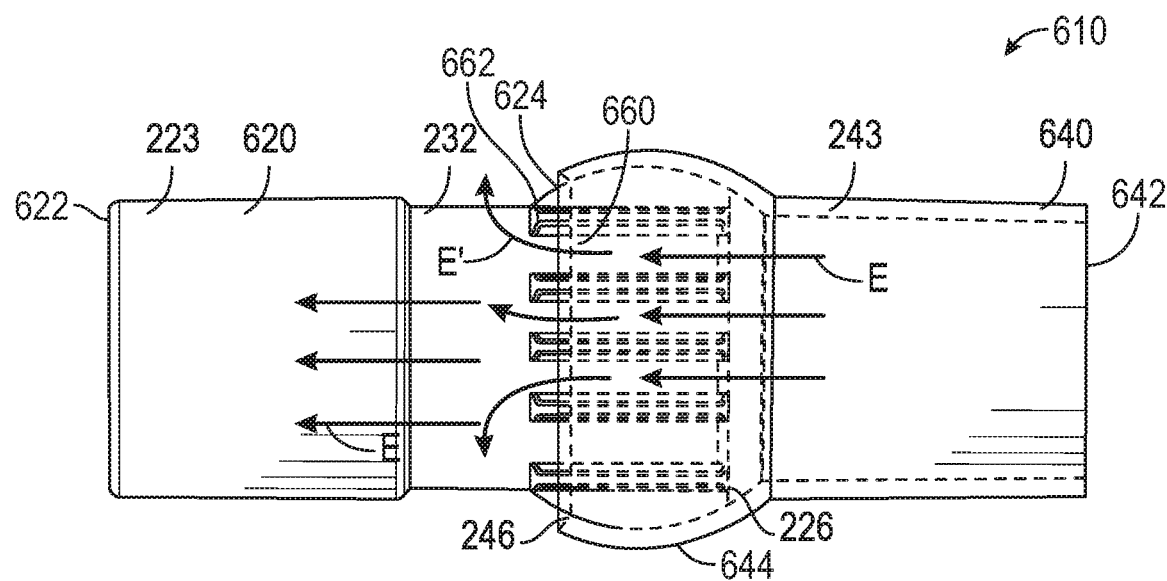
FIG. 6B is a top plan view of the leakage component of FIG. 6A, in accordance with various aspects of the present disclosure.

FIG. 6A is a perspective view of a leakage component 610 with a patient-side tubular housing 640 shown in broken lines, in accordance with various aspects of the present disclosure. FIG. 6B is a top plan view of the leakage component 610 of FIG. 6A, in accordance with various aspects of the present disclosure. The leakage component 610 includes features that are similar to the leakage component 210, as previously described. Therefore, unless noted, similar features are identified by similar reference numerals. With reference to FIGS. 6A and 6B, the leakage component 610 allows for intentional leakage between the ball joint surface 624 and the socket 644.

In the depicted example, the ball joint surface 624 includes a plurality of fluid diversion channels or channel walls 662 extending from the ball joint surface 624. As illustrated, the channel walls 662 define fluid diversion channels or axial flow channels 660 therebetween. In some embodiments, the outermost portions of the channel walls 662 can form an overall arcuate, spherical, or rounded profile to engage with the socket 644 of the patient-side tubular housing 640. Optionally, the channel walls 662 can be parallel to each other. In some embodiments, the channel walls 662 can be radially arranged.

As illustrated, a portion of the ventilator-side tubular housing 620 can be disposed within the patient-side tubular housing 640 to permit at least a portion of the plurality of channel walls 662 extending from the ball joint surface 624 mate or engage with the socket 644. As can be appreciated, the axial flow channels 660 defined between the ball joint surface 624 and the socket 644 can allow for a controlled leak rate from the interior flow path defined within the leakage component 610.

During operation, the axial flow channels 660 can direct flow through the leakage component 610. For example, during expiration, bulk expiratory flow (E) is directed through the patient-side tubular housing 640. A portion of the bulk expiratory flow (E'), which can include carbon dioxide, is directed out of the axial flow channels 660. Further, by disposing the axial flow channels 660 along the ball joint surface 624, inspiratory flow (I) may be diverted away from the axial flow channels 660. For example, during inspiration, the leakage component 610 defines a flow path that guides inspiratory flow (I) from the ventilator-side opening 622 to the patient-side opening 642, while bypassing the axial flow channels 660 disposed along the ball joint surface 624.

Figure 7:
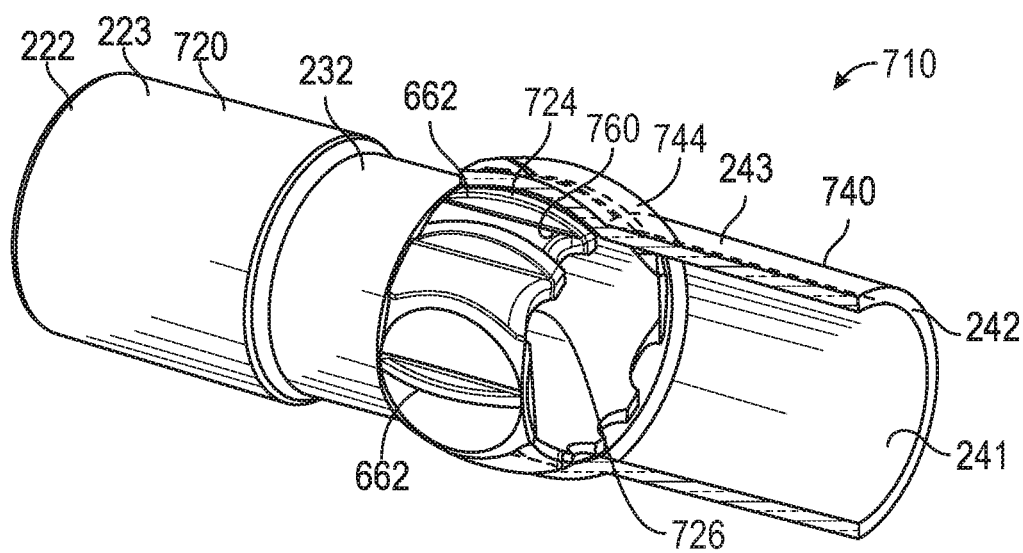
FIG. 7 is a partial cross-sectional perspective view of a leakage component, in accordance with various aspects of the present disclosure.

FIG. 7 is a partial cross-sectional perspective view of a leakage component 710, in accordance with various aspects of the present disclosure. The leakage component 710 includes features that are similar to the leakage component 210, as previously described. Therefore, unless noted, similar features are identified by similar reference numerals. In the depicted example, the leakage component 710 includes ball joint surface 724 has a distal end portion having a scalloped or undulating ball joint edge 726. The ball joint edge 726 can maintain intentional leakage between the ball joint surface 724 and the socket 744.

As can be appreciated, the undulating ball joint edge 726 can reduce the variability of leakage flow as the patient-side tubular housing 740 is moved relative to the ventilator-side tubular housing 720. As the patient-side tubular housing 740 is bent relative to the ventilator-side tubular housing 720, the undulating ball joint edge 726 allows the entrance or exit flow paths to the axial flow channels 760 to remain unobstructed. Further, the arrangement of the ball joint edge 726 may allow for the patient-side tubular housing 740 to rotate more easily relative to the ventilator-side tubular housing 720. In some applications, the arrangement of the ball joint edge 726 may facilitate the engagement and/or disengagement of the ball joint surface 724 and the socket 744.

Figure 8:
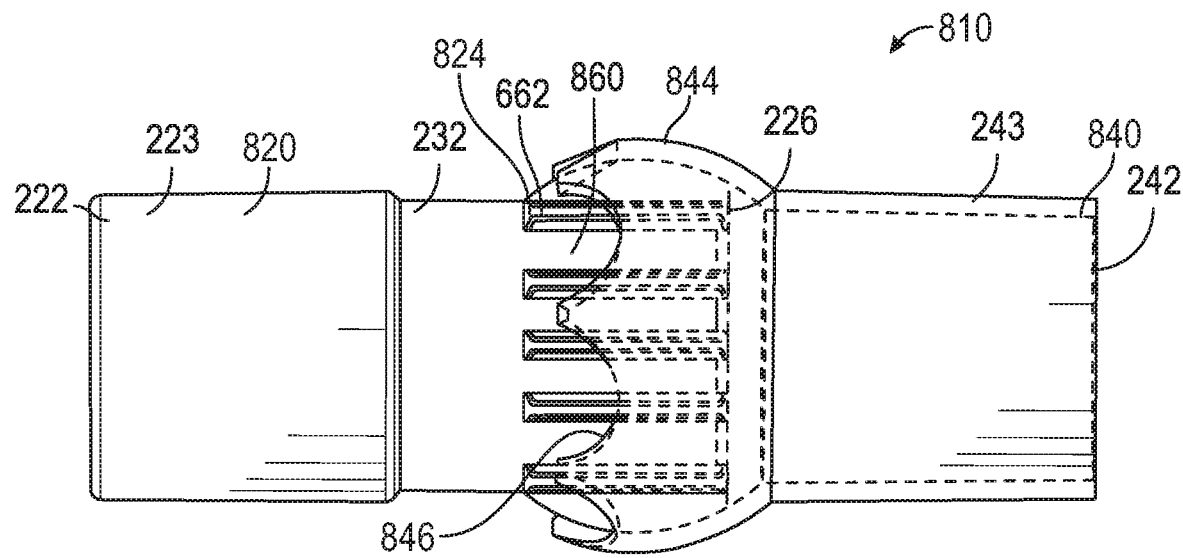
FIG. 8 is a top plan view of a leakage component with a patient-side tubular housing shown in broken lines, in accordance with various aspects of the present disclosure.

FIG. 8 is a top plan view of a leakage component 810 with a patient-side tubular housing 840 shown in broken lines, in accordance with various aspects of the present disclosure. The leakage component 810 includes features that are similar to the leakage component 210, as previously described. Therefore, unless noted, similar features are identified by similar reference numerals. In the depicted example, the leakage component 810 includes socket 844 having a scalloped or undulating socket edge 846 at a distal end portion to maintain intentional leakage between the ball joint surface 824 and the socket 844.

In some embodiments, the undulating socket edge 846 can reduce the variability of leakage flow as the patient-side tubular housing 840 is moved relative to the ventilator-side tubular housing 820. As the patient-side tubular housing 840 is bent relative to the ventilator-side tubular housing 820, the undulating socket edge 846 allows the entrance or exit flow paths to the axial flow channels 860 to remain unobstructed. Further, the arrangement of the socket edge 846 may allow for the patient-side tubular housing 840 to rotate more easily relative to the ventilator-side tubular housing 820. In some applications, the arrangement of the socket edge 846 may facilitate the engagement and/or disengagement of the ball joint surface 824 and the socket 844.

In some embodiments, the ventilator-side tubular housing 720, 820 and the patient-side tubular housing 740, 840 can both have scalloped or undulating edges. For example, a ventilator-side tubular housing 720, 820 can be coupled with a patient-side tubular housing 740, 840, wherein the ventilator-side tubular housing 720, 820 comprises a scalloped or undulating ball joint edge 726, and the patient-side tubular housing 740, 840 comprises a scalloped or undulating socket edge 846.

Figure 9:
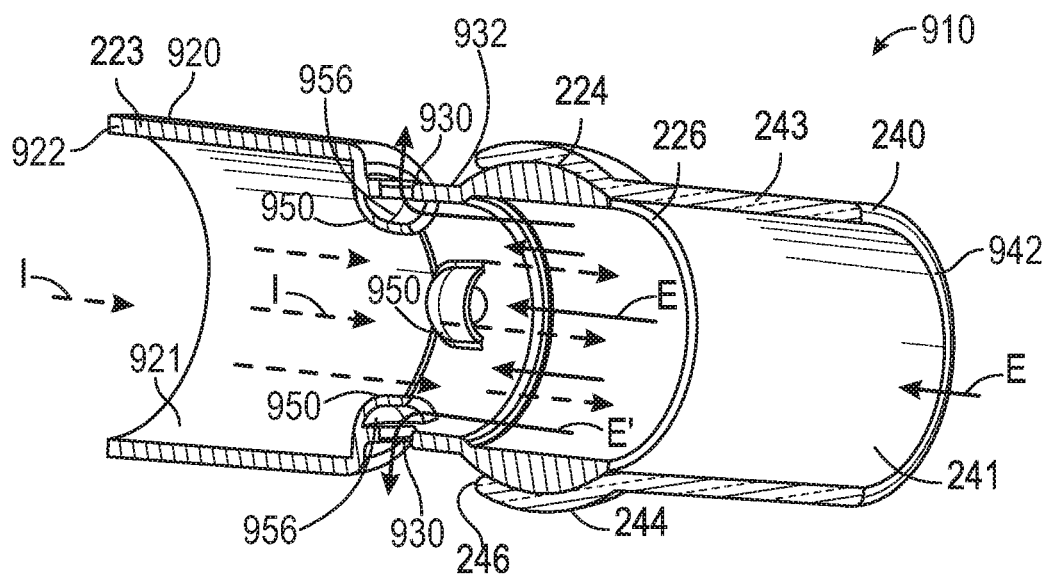
FIG. 9 is a cross-sectional perspective view of a leakage component, in accordance with various aspects of the present disclosure.

FIG. 9 is a cross-sectional perspective view of a leakage component 910, in accordance with various aspects of the present disclosure. The leakage component 910 includes features that are similar to the leakage component 210, as previously described. Therefore, unless noted, similar features are identified by similar reference numerals. In the depicted example, the leakage component 910 can include leakage ports 930 shrouded by individual fluid diversion members 950.

As illustrated, the ventilator-side tubular housing 920 can include one or more leakage ports 930 formed through the ventilator-side tubular housing 920. The leakage ports 930 can be circumferentially disposed around the recessed area 932. Optionally, the leakage ports 930 can be equidistantly spaced about the ventilator-side tubular housing 920. In some embodiments, the leakage ports 930 can have a generally circular profile.

In some embodiments, individual fluid diversion members 950 can extend from the inner surface 921 so that each leakage port 930 is enshrouded by a respective fluid diversion members. The fluid diversion members 950 can have a generally semi-spherical shape or "igloo" shape, defining a fluid diversion cavity 956 between the leakage port 930 and a surface of the fluid diversion members 950 opposite the leakage port 930. During operation, the fluid diversion members 950 interact with the flow through the leakage component 910. For example, during expiration, the geometry of the fluid diversion members 950 defines a flow path that guides a portion of the expiratory flow (E') toward a respective leakage port 930. Further, during inspiration, the geometry of the fluid diversion members 950 defines a flow path that guides inspiratory flow (I) from the ventilator-side opening 922 to the patient-side opening 942, bypassing or otherwise guiding inspiratory flow away from the leakage ports 930.

Figure 10A:
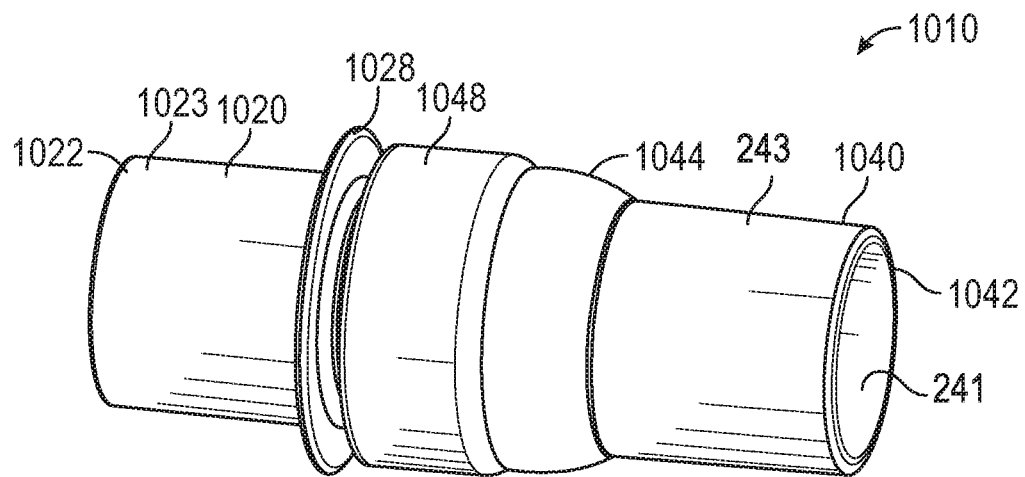
FIG. 10A is a perspective view of a leakage component, in accordance with various aspects of the present disclosure.
Figure 10B:
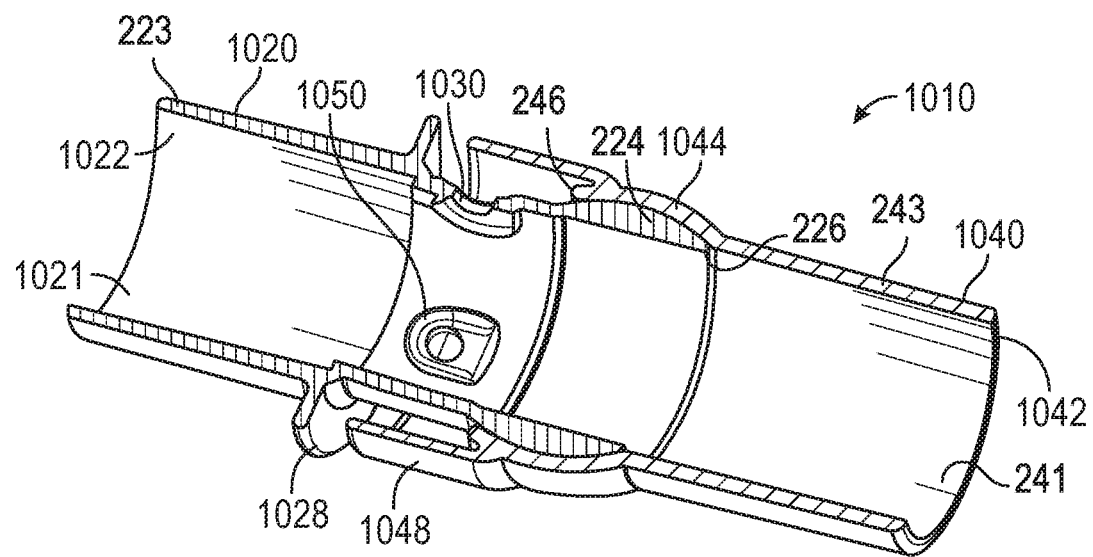
FIG. 10B is a cross-sectional perspective view of the leakage component of FIG. 10A, in accordance with various aspects of the present disclosure.

FIG. 10A is a perspective view of a leakage component 1010, in accordance with various aspects of the present disclosure. FIG. 10B is a cross-sectional perspective view of the leakage component 1010 of FIG. 10A, in accordance with various aspects of the present disclosure. The leakage component 1010 includes features that are similar to the leakage component 210, as previously described. Therefore, unless noted, similar features are identified by similar reference numerals. In the depicted example, the leakage component 1010 includes a shroud 1048 to provide additional sound reduction and fluid diversion.

As illustrated, the patient-side tubular housing 1040 can include a shroud 1048 extending from the socket 1044. The shroud 1048 extends from the socket 1044, in a direction that is generally opposite to the patient-side opening 1042. In some embodiments, the shroud 1048 can have a generally cylindrical shape. The shroud 1048 extends over at least a portion of the leakage ports 1030. When the patient-side tubular housing 1040 is coupled with a ventilator-side tubular housing 1020, the shroud 1048 is positioned circumferentially around a portion of the socket 1044.

In the depicted example, the shroud 1048 axially extends over a portion of the ventilator-side tubular housing 1020, including at least a portion of the leakage ports 1030. Optionally, the shroud 1048 can be radially spaced apart from the leakage ports 1030 of the ventilator-side tubular housing 1020. In some embodiments, the shroud 1048 extends from the ventilator-side tubular housing 1020.

During operation, the shroud 1048 can direct leakage flow from the leakage ports 1030 to move in an axial direction along the outer surface 1023 of the ventilator-side tubular housing 1020. When fluid moves out of a leakage ports 1030, the fluid is redirected by the shroud 1048 to move in a direction that is away from the patient-side opening 1042. By directing the fluid moving out of the leakage ports 1030 away from the patient-side opening 1042, disturbances caused by the fluid leaking from the leakage component 1010 are prevented.

Optionally, a rib 1028 extending from the outer surface 1023 can further divert and/or diffuse the leakage flow. The rib 1028 extends away from an outer surface of any of the ventilator-side tubular housing or the patient-side tubular housing 1040. As illustrated, the rib 1028 can be axially spaced apart from the end of the shroud 1048.

As illustrated, the ventilator-side tubular housing 1020 can include fluid diversion member 1050 extending from the inner surface 1021 into the flow path and encircling at least a portion of a leakage port 1030. Each leakage port 1030 can include a respective fluid diversion member 1050. The fluid diversion members 1050 can have a generally U-shaped walls having a closed first end portion and an open second end portion. The leakage ports 1030 are positioned with the open second end portion between the respective leakage port 1030 and the patient-side opening 1042. The closed first end portion is positioned between the respective leakage port 1030 and the ventilator-side tubular housing 1020.

During operation, the fluid diversion members 1050 interact with the flow through the leakage component 1010. For example, during expiration, the geometry of the fluid diversion members 1050 defines a flow path that guides expiratory flow toward a respective leakage port 1030. Further, during inspiration, the walls of the fluid diversion members 1050 define a flow path that guides inspiratory flow from the ventilator-side opening 1022 to the patient-side opening 1042, while diverting the inspiratory flow away from the leakage ports 1030.

Figure 11A:
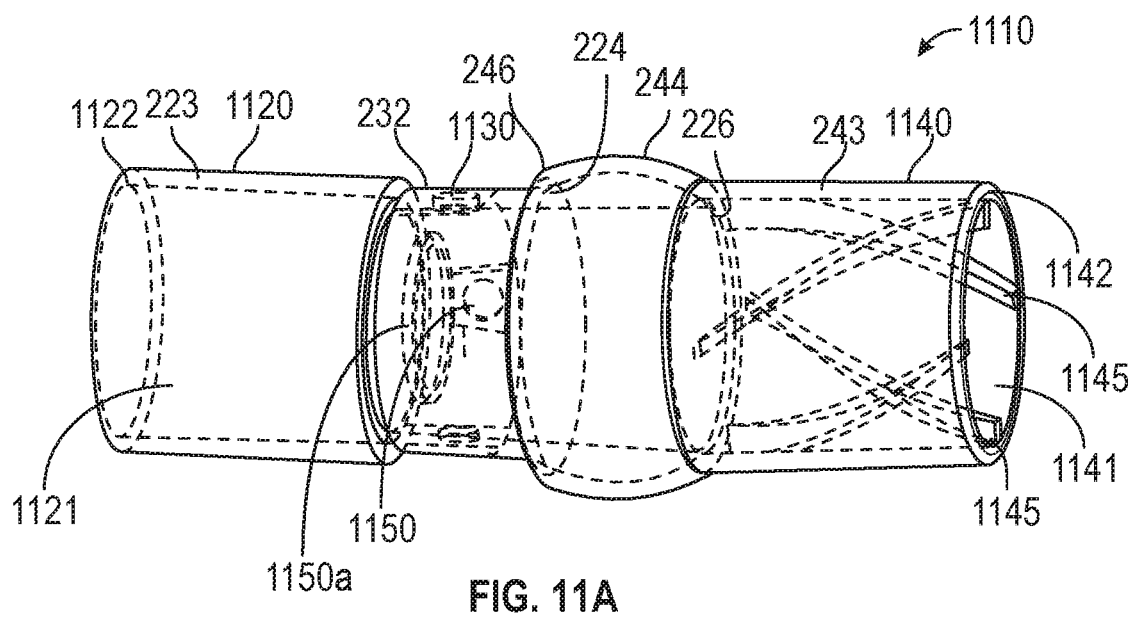
FIG. 11A is a perspective view of a leakage component with a ventilator-side tubular housing and a patient-side tubular housing shown in broken lines, in accordance with various aspects of the present disclosure.
Figure 11B:
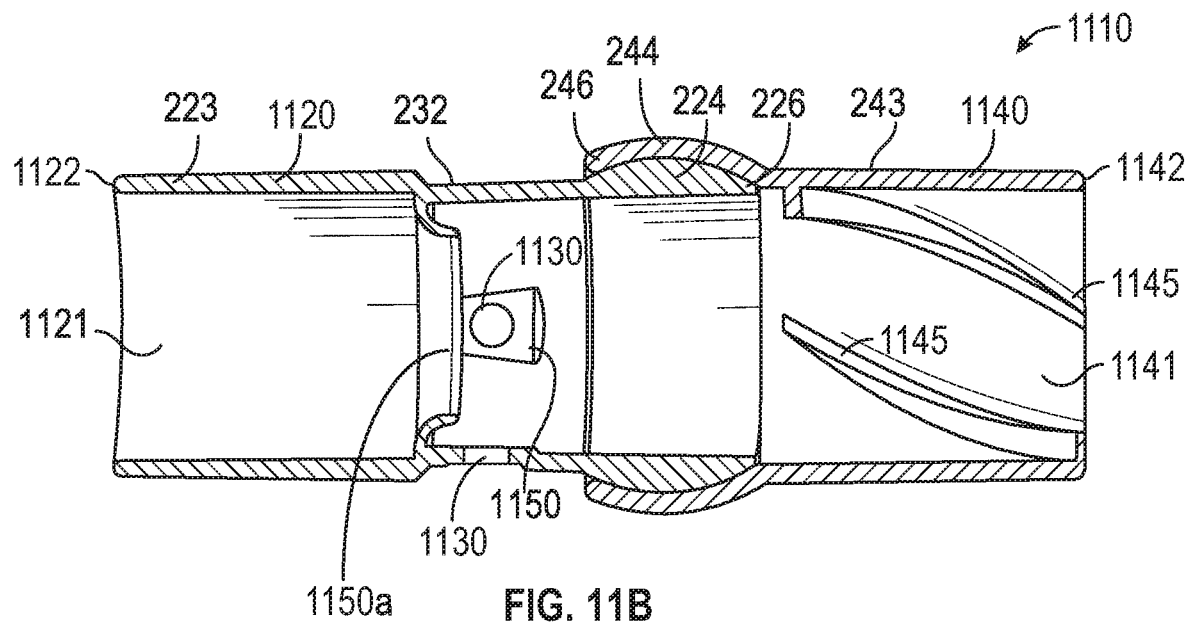
FIG. 11B is a cross-sectional elevation view of the leakage component of FIG. 11A, in accordance with various aspects of the present disclosure.

FIG. 11A is a perspective view of a leakage component 1110 with a ventilator-side tubular housing 1120 and a patient-side tubular housing 1140, in accordance with various aspects of the present disclosure. FIG. 11B is a cross-sectional elevation view of the leakage component 1110 of FIG. 11A, in accordance with various aspects of the present disclosure. The leakage component 1110 includes features that are similar to the leakage component 210, as previously described. Therefore, unless noted, similar features are identified by similar reference numerals. In the depicted example, the leakage component 1110 includes vanes 1145 to induce swirl of a fluid moving through the flow path through the leakage component 1110 and enhance leakage flow out of the leakage component 1110.

As illustrated, the patient-side tubular housing 1140 includes one or more vanes 1145 extending from the inner surface 1141 of the patient-side tubular housing 1140. In some embodiments, the vanes 1145 extend axially from the patient-side opening 1142 toward the ventilator-side tubular housing 1120. Optionally, the vanes 1145 have a generally helical or spiral arrangement within the patient-side tubular housing 1140. Advantageously, the vanes 1145 can induce swirl in the expiratory flow to augment leakage flow through the leakage ports 1130.

In the depicted example, the leakage ports 1130 are formed through the ventilator-side tubular housing 1120. As can be appreciated, during expiratory flow, the leakage ports 1130 are downstream of the vanes 1145, therefore allowing the leakage ports 1130 to receive swirled or turbulent expiratory flow, augmenting leakage flow through the leakage ports 1130. In some embodiments, the leakage ports 1130 can have a generally circular cross-sectional profile. Optionally, the leakage ports 1130 can be radially defined through the ventilator-side tubular housing 1120. In some embodiments, the leakage ports 1130 can be formed at an angle relative to the direction of flow through the ventilator-side tubular housing 1120.

Optionally, individual fluid diversion members 1150 can be disposed surrounding at least a portion of the leakage ports 1130 or adjacent to the leakage ports 1130. The fluid diversion members 1150 can have a generally flattened surface that extends axially and/or radially around each respective leakage port 1130. In some embodiments, the fluid diversion members 1150 can have a generally trapezoidal (or "bullnose") shape that tapers from a wider portion to a narrower portion. Optionally, a wider portion of the fluid diversion member 1150 can be disposed toward the patient-side tubular housing 1140. Further, a narrower portion of the fluid diversion member 1150 can be disposed opposite to the wider portion of the fluid diversion member 1150. Advantageously, the fluid diversion members 1150 can disrupt the boundary layer of axial flow through the ventilator-side tubular housing 1120, producing a direction-dependent leak rate differential.

Further, in some embodiments, the leakage component 1110 can include a secondary fluid diversion member 1150*a*. The secondary fluid diversion member 1150*a* can similarly be disposed around or adjacent to the leakage ports 1130. As illustrated, the secondary fluid diversion member 1150*a* is axially spaced apart from the individual fluid diversion members 1150. The secondary fluid diversion member 1150*a* can axially and/or radially extend from the inner surface 1121. In some embodiments, the secondary fluid diversion member 1150*a* can be circumferentially disposed around the entire circumference of the ventilator-side tubular housing 1120. In some embodiments, the secondary fluid diversion member 1150*a* can be circumferentially disposed around one or more portions of the circumference of the ventilator-side tubular housing 1120.

During operation, vanes 1145, individual fluid diversion members 1150, and secondary fluid diversion members 1150*a* can interact with the flow through the leakage component 1110. For example, during expiration, the vanes 1145 can induce swirl or turbulence into the bulk expiratory flow as the flow travels toward the leakage ports 1130. A portion of the bulk expiratory flow can be directed into the leakage ports 1130 by the individual fluid diversion members 1150 and the secondary fluid diversion members 1150*a*. Further, during inspiration, the individual fluid diversion members 1150, and secondary fluid diversion members 1150*a* can guide the bulk inspiratory flow from the ventilator-side opening 1122 to the patient-side opening 1142 and over the leakage ports 1130, bypassing or otherwise guiding bulk inspiratory flow away from the leakage ports 1130. For example, as bulk inspiratory flow encounters the secondary fluid diversion members 1150*a*, the flow can be accelerated due to the nozzle effect provided by the secondary fluid diversion members 1150, producing a low pressure area in the vicinity surrounding the leakage ports 1130. The individual fluid diversion members 1150 can further disrupt flow vectors in the vicinity of the leakage ports 1130, since flow is disproportionately directed towards the larger voids between the leakage ports 1130, guiding inspiratory flow away from the leakage ports 1130. Optionally, the vanes 1145 can induce swirl or turbulence into the bulk inspiratory flow.

Figure 12A:
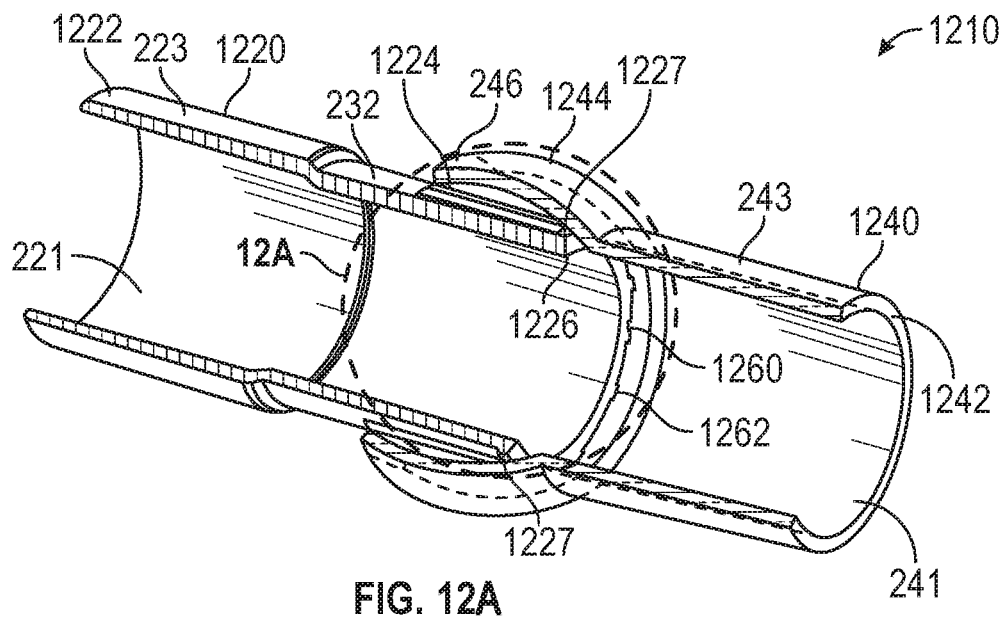
FIG. 12A is a cross-sectional perspective view of a leakage component, in accordance with various aspects of the present disclosure.
Figure 12B:
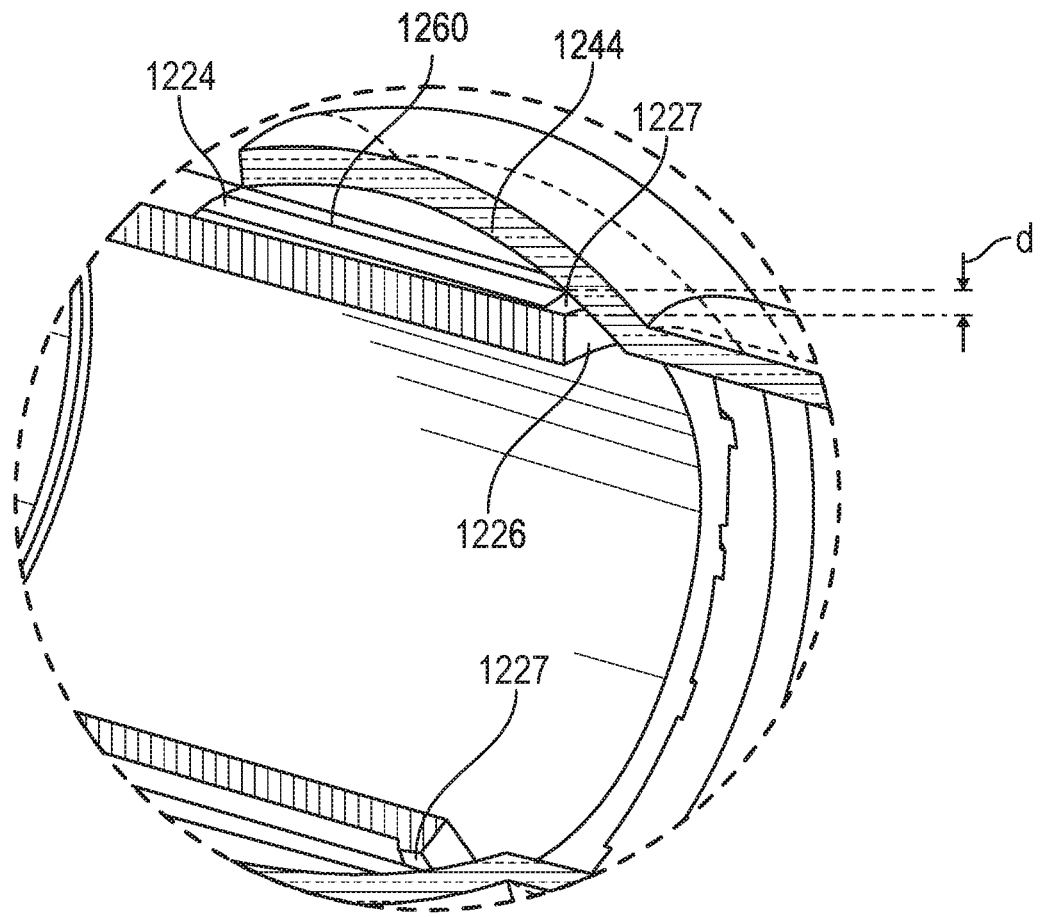
FIG. 12B is a detailed view of the leakage component of FIG. 12A, in accordance with various aspects of the present disclosure.

FIG. 12A is a cross-sectional perspective view of a leakage component 1210, in accordance with various aspects of the present disclosure. FIG. 12B is a detailed view of the leakage component 1210 of FIG. 12A, in accordance with various aspects of the present disclosure. With reference to FIGS. 12A and 12B, the leakage component 1210 includes features that are similar to the leakage component 210, as previously described. Therefore, unless noted, similar features are identified by similar reference numerals. With reference to FIG. 12A, the leakage component 1210 allows for intentional leakage between the ball joint surface 1224 and the socket 1244.

In the depicted example, the ball joint surface 1224 includes a plurality of fluid diversion channels or channel walls 1262 extending from the ball joint surface 1224. As illustrated, the channel walls 1262 define fluid diversion channels or axial flow channels 1260 therebetween. In some embodiments, the outermost portions of the channel walls 1262 can form an overall arcuate, spherical, or rounded profile to engage with the socket 1244 of the patient-side tubular housing 1240.

In the depicted example, the ball joint surface 1224 includes a fluid diversion rib or flow control rib 1227 extending radially from the ball joint edge 1226. As illustrated, the flow control rib 1227 extends radially outward toward the inner surface of the socket 1244 to control the leakage flow from the axial flow channels 1260. As can be appreciated, by defining the distance (d) between the flow control rib 1227 and the socket 1244, the leakage component 1210 can tightly control the leakage rate of the axial flow channels 1260 and the variability of the leakage rate during relative movement of the ventilator-side tubular housing 1220 relative to the patient-side tubular housing 1240. In some embodiments, the distance (d) can be selected for a desired leakage rate by a designer or manufacturer in response to experimentation and/or computational fluid dynamic (CFD) analysis.

For example, during expiration, the portion of bulk expiratory flow that is directed through the axial flow channels 1260 can be controlled or regulated by the geometry and/or positioning of the flow control rib 1227. Further, during inspiration, the flow control rib 1227 may divert inspiratory flow away from the axial flow channels 1260 and guide flow from the ventilator-side opening 1222 to the patient-side opening 1242.

Figure 13A:
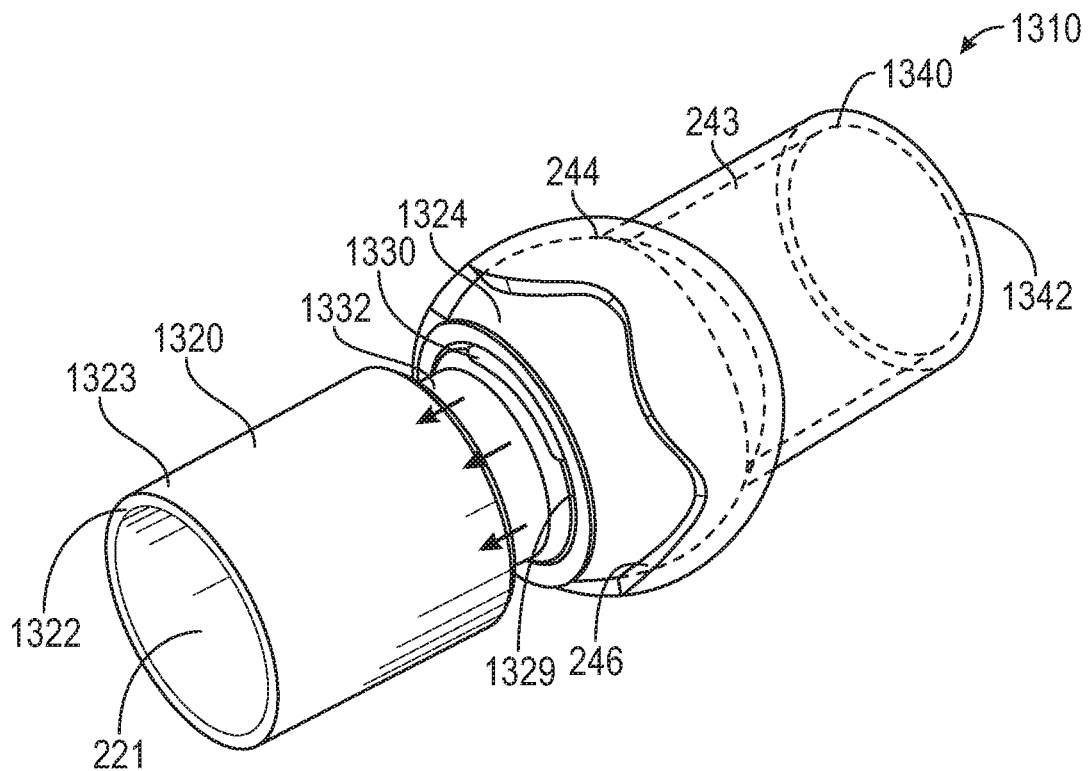
FIG. 13A is a perspective view of a leakage component with a patient-side tubular housing shown in broken lines, in accordance with various aspects of the present disclosure.
Figure 13B:
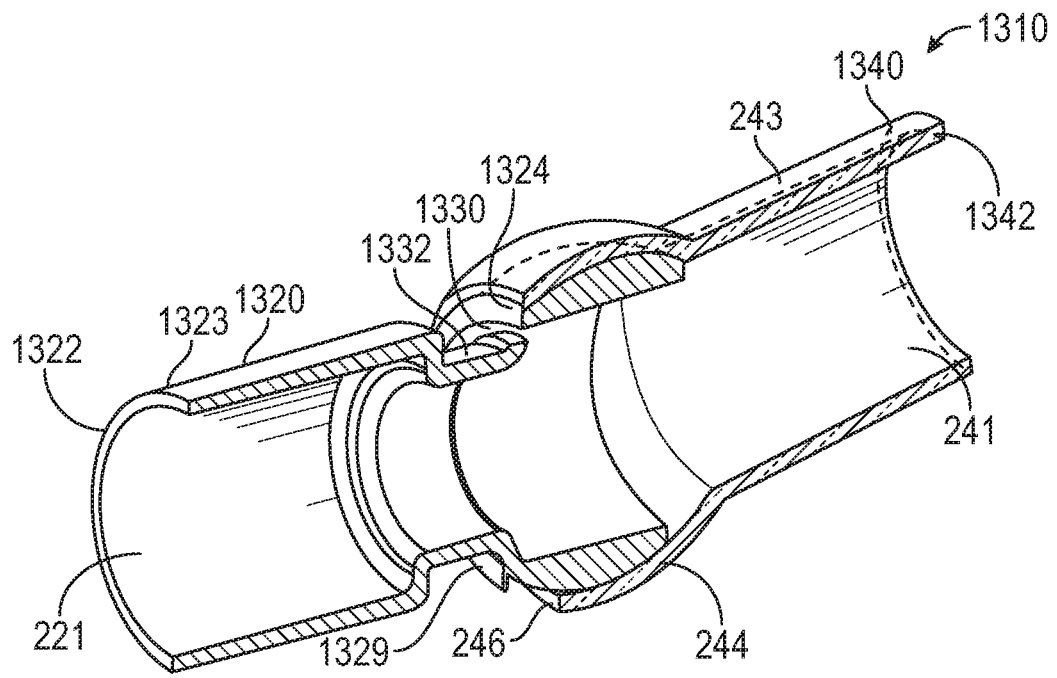
FIG. 13B is a cross-sectional perspective view of the leakage component of FIG. 13A, in accordance with various aspects of the present disclosure.
Figure 13C:
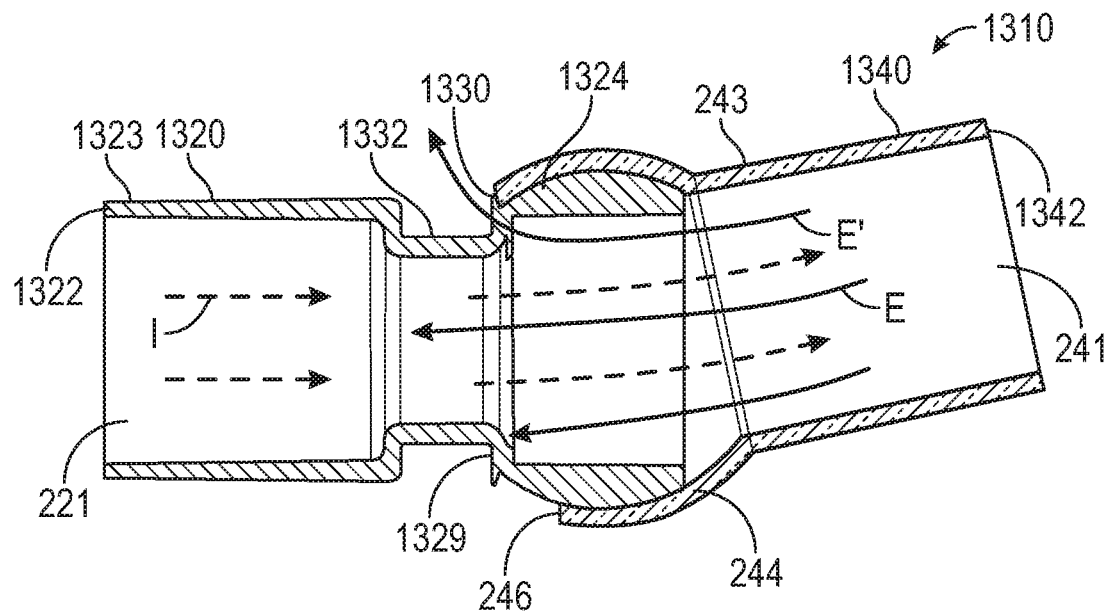
FIG. 13C is a cross-sectional elevation view of the leakage component of FIG. 13A, in accordance with various aspects of the present disclosure.

FIG. 13A is a perspective view of a leakage component 1310 with a patient-side tubular housing 1340 shown in broken lines, in accordance with various aspects of the present disclosure. FIG. 13B is a cross-sectional perspective view of the leakage component 1310 of FIG. 13A, in accordance with various aspects of the present disclosure. FIG. 13C is a cross-sectional elevation view of the leakage component 1310 of FIG. 13A, in accordance with various aspects of the present disclosure. The leakage component 1310 includes features that are similar to the leakage component 210, as previously described. Therefore, unless noted, similar features are identified by similar reference numerals. With reference to FIGS. 13A-13C, the leakage component 1310 includes leakage ports 1330 configured to direct leakage flow in an axial direction.

As illustrated, the ventilator-side tubular housing 1320 includes leakage ports 1330 adjacent to a shoulder 1329. In some embodiments, the shoulder 1329 extends radially from the recessed area 1332. Optionally, the shoulder 1329 can have a radius that is the same or similar as the radius of the outer surface 1323 of the ventilator-side tubular housing 1320. Further, in some embodiments, the shoulder 1329 can extend toward the ball joint surface 1324 to define an edge of the ball joint surface 1324.

In some embodiments, the leakage ports 1330 are circumferentially disposed along the shoulder 1329. The leakage ports 1330 can be disposed along the entire circumference of the shoulder 1329 or a portion of the circumference of the shoulder 1329. For example, the leakage ports 1330 can be disposed along 180 degrees of the circumference of the shoulder 1329. As can be appreciated, the leakage ports 1330 can be disposed along approximately 170 degrees of the circumference, 150 degrees of the circumference, 120 degrees of the circumference, 90 degrees of the circumference, 60 degrees of the circumference, etc.

Optionally, the leakage ports 1330 can be generally formed as arcuate slots. The leakage ports 1330 can each have an angular length of 100 degrees, 90 degrees, 75 degrees, 60 degrees, 45 degrees, 30 degrees, 15 degrees, etc. The leakage ports 1330 can be angularly spaced apart with angular spacing of 100 degrees, 90 degrees, 75 degrees, 60 degrees, 45 degrees, 30 degrees, 15 degrees, etc.

Advantageously, by disposing the leakage ports 1330 along the shoulder 1329, leakage flow exiting the leakage ports 1330 can exit the leakage component 1310 in an axial direction and away from the patient and/or care giver. Further, by disposing the leakage ports 1330 on the shoulder

1329, inspiratory flow (I) may be diverted away from the leakage ports 1330. For example, during inspiration, the leakage component 1310 defines a flow path that guides inspiratory flow (I) from the ventilator-side opening 1322 to the patient-side opening 1342, while bypassing the leakage ports 1330 disposed within the shoulder 1329. Further, during expiration, the arrangement of the shoulder 1329 within the leakage component 1310 places the leakage ports 1330 parallel to the expiratory flow (E), allowing for a portion of the expiratory flow (E') to enter the leakage ports 1330.

Figure 14A:
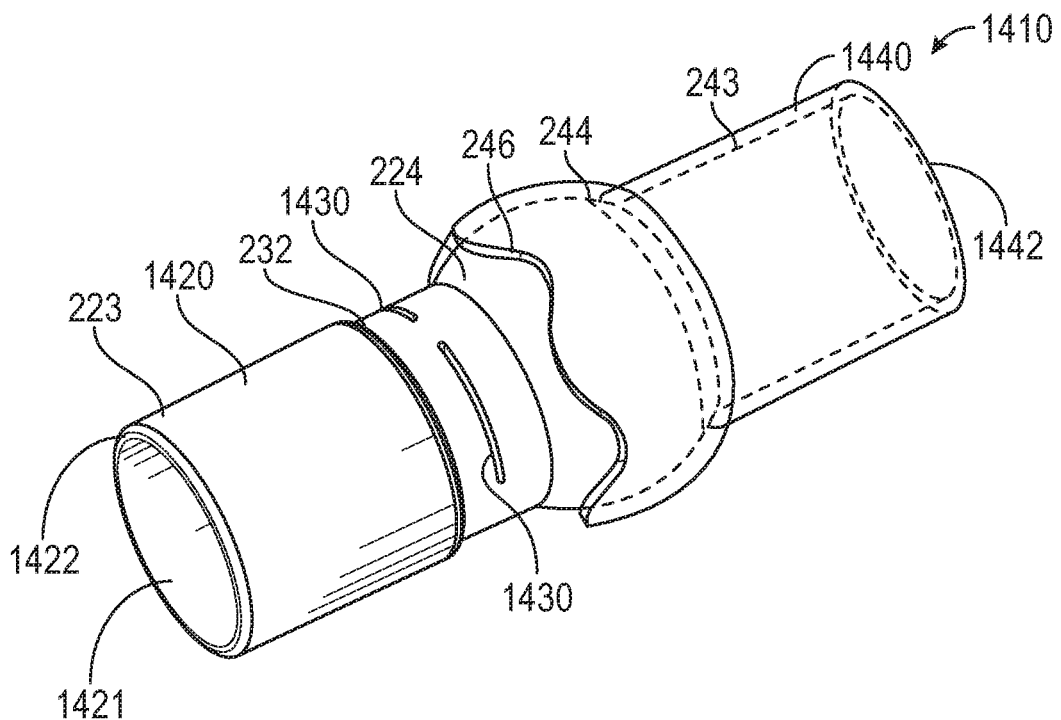
FIG. 14A is a perspective view of a leakage component with a patient-side tubular housing shown in broken lines, in accordance with various aspects of the present disclosure.
Figure 14B:
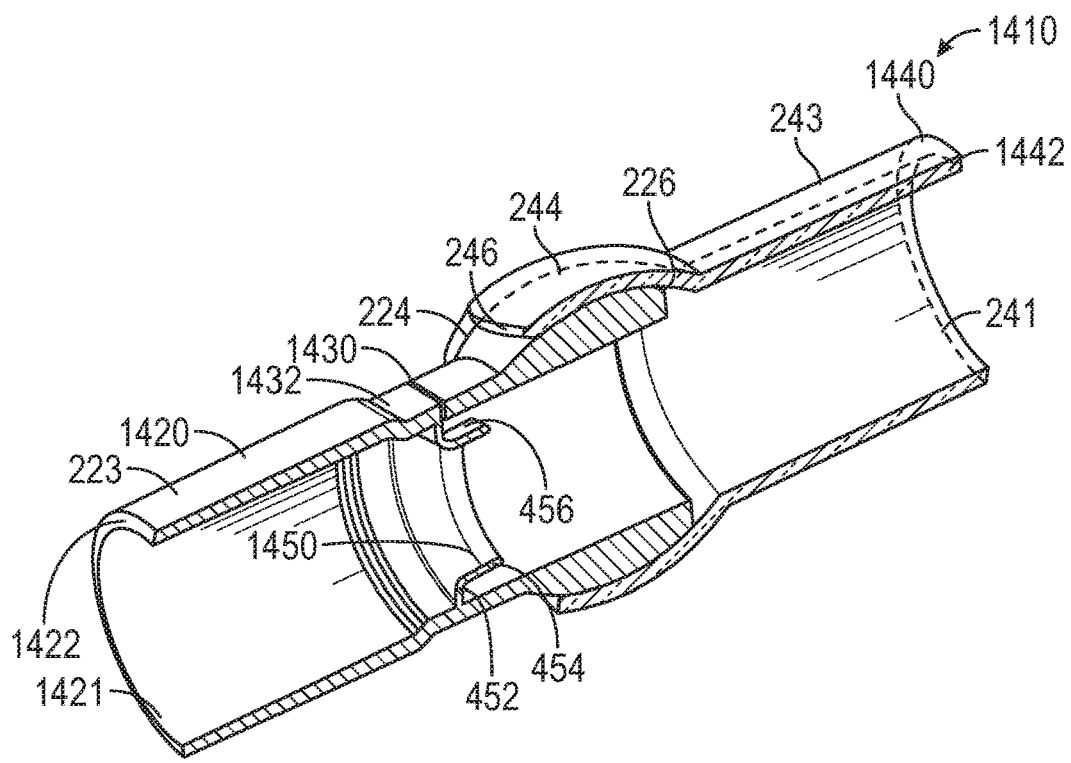
FIG. 14B is a cross-sectional perspective view of the leakage component of FIG. 14A, in accordance with various aspects of the present disclosure.

FIG. 14A is a perspective view of a leakage component 1410 having a ventilator-side tubular housing 1420 and a patient-side tubular housing 1440, in accordance with various aspects of the present disclosure. FIG. 14B is a cross-sectional perspective view of the leakage component 1410 of FIG. 14A, in accordance with various aspects of the present disclosure. The leakage component 1410 includes features that are similar to the leakage component 210, as previously described. Therefore, unless noted, similar features are identified by similar reference numerals. In the depicted example, the leakage component 1410 includes leakage ports 1430 configured to enhance entrainment during operation.

As illustrated, the leakage component 1410 includes leakage ports 1430 that are disposed along the ventilator-side tubular housing 1420. In the depicted example, the leakage ports 1430 are disposed transverse or perpendicular to the direction of flow through the ventilator-side tubular housing 1420. Optionally, the leakage ports 1430 are disposed within the recessed area 1432.

The leakage ports 1430 can be disposed along the entire circumference of the ventilator-side tubular housing 1420 or a portion of the circumference. For example, the leakage ports 1430 can be disposed along 180 degrees of the circumference of the ventilator-side tubular housing 1420. As can be appreciated, the leakage ports 1430 can be disposed along approximately 170 degrees of the circumference, 150 degrees of the circumference, 120 degrees of the circumference, 90 degrees of the circumference, 60 degrees of the circumference, etc.

As illustrated, the leakage ports 1430 can be generally formed as arcuate slots. The leakage ports 1430 can each have an angular length of 100 degrees, 90 degrees, 75 degrees, 60 degrees, 45 degrees, 30 degrees, 15 degrees, etc. The leakage ports 1430 can be angularly spaced apart with angular spacing of 100 degrees, 90 degrees, 75 degrees, 60 degrees, 45 degrees, 30 degrees, 15 degrees, etc.

As illustrated, the ventilator-side tubular housing 1420 can include a fluid diversion member 1450 extending from the inner surface 1421. The fluid diversion member 1450 can extend circumferentially around the leakage ports 1430. During operation, the fluid diversion member 1450 interacts with the flow through the leakage component 1410. For example, during expiration, the geometry of the fluid diversion member 1450 defines a flow path that guides expiratory flow toward the leakage ports 1430. As can be appreciated, the arcuate slot geometry of the leakage ports 1430 can allow for improved or enhanced entrainment of ambient or adjacent air flow. Further, during inspiration, the fluid diversion member 1450 defines a flow path that guides inspiratory flow from the ventilator-side opening 1422 to the patient-side opening 1442, while diverting the inspiratory flow away from the leakage ports 1430.

Figure 15:
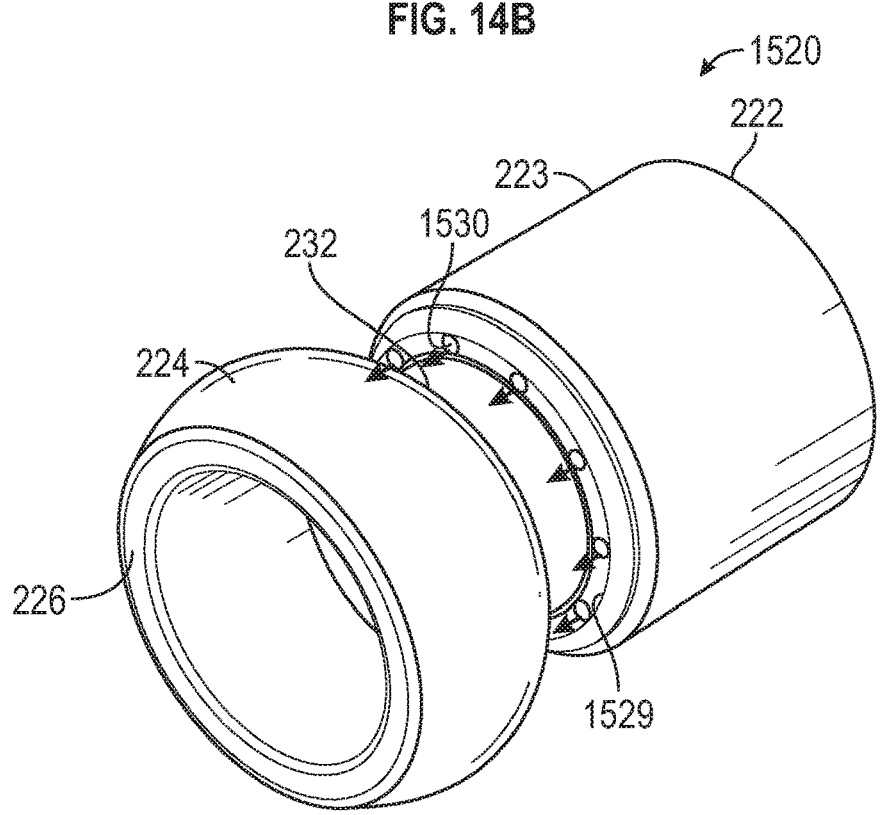
FIG. 15 is a perspective view of a ventilator-side tubular housing, in accordance with various aspects of the present disclosure.

FIG. 15 is a perspective view of a ventilator-side tubular housing 1520, in accordance with various aspects of the present disclosure. The ventilator-side tubular housing 1520 includes features that are similar to the ventilator-side tubular housing 1320, as previously described. Therefore, unless noted, similar features are identified by similar reference numerals. In the depicted example, the ventilator-side tubular housing 1520 includes leakage ports 1530 configured to direct leakage flow in an axial direction.

As illustrated, the ventilator-side tubular housing 1520 includes leakage ports 1530 disposed on a shoulder 1529. By disposing the leakage ports 1530 along the shoulder 1529, the leakage ports 1530 can be disposed parallel to flow through the ventilator-side tubular housing 1520. In some embodiments, the leakage ports 1530 are circumferentially disposed along the shoulder 1529.

The leakage ports 1530 can be disposed along the entire circumference of the shoulder 1529 or a portion of the circumference of the shoulder 1529. For example, the leakage ports 1530 can be disposed along 180 degrees of the circumference of the shoulder 1529. As can be appreciated, the leakage ports can be disposed along approximately 170 degrees of the circumference, 150 degrees of the circumference, 120 degrees of the circumference, 90 degrees of the circumference, 60 degrees of the circumference, etc. In the depicted example, the leakage ports 1530 can have a generally circular profile. The leakage ports 1530 can be angularly spaced apart with angular spacing of 100 degrees, 90 degrees, 75 degrees, 60 degrees, 45 degrees, 30 degrees, 15 degrees, etc.

As can be appreciated, embodiments of leakage components herein include components or portions that may be combined with components or portions of other embodiments of leakage components. In some applications, various components may be selectable by a user to be combined in a clinical setting to provide desired characteristics, such as leak rates, directional flow behavior, etc. For example, certain patient-side tubular housings of some embodiments may be combined with or coupled with ventilator-side tubular housings of some embodiments.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A leakage component, comprising: a first tubular housing defining a first flow path between a first end portion and a second end portion; and a plurality of leakage ports formed in the first housing and in fluid communication with the first flow path, wherein fluid flow through the plurality of leakage ports is configured to entrain ambient air into the fluid flow exiting the plurality of leakage ports to decelerate the fluid flow.

Clause 2. The leakage component of Clause 1, further comprising a fluid diversion member extending from the first housing and disposed adjacent to one or more leakage ports of the plurality of leakage ports, wherein the fluid diversion member is configured to divert fluid flow away from the one or more leakage ports in a first flow direction and to direct fluid flow toward the one or more leakage ports in a second flow direction.

Clause 3. The leakage component of Clause 2, wherein the fluid diversion member extends radially into the first flow path and extends axially to enshroud the one or more leakage ports.

Clause 4. The leakage component of Clause 3, wherein an outer surface of the fluid diversion member defines an inspiration flow path between the first end portion and the second end portion, and an inner surface of the fluid diversion member defines a partial expiration flow path between the second end portion and the one or more leakage ports.

Clause 5. The leakage component of Clause 3 or 4, wherein the fluid diversion member enshrouds the plurality of leakage ports.

Clause 6. The leakage component of any of Clauses 3-5, wherein the fluid diversion member extends an axial length to at least partially axially overlap the one or more leakage ports.

Clause 7. The leakage component of any of Clauses 3-6, wherein the fluid diversion member extends an axial length to axially overlap the one or more leakage ports.

Clause 8. The leakage component of any of Clauses 2-7, wherein the fluid diversion member extends around a circumference of the first housing.

Clause 9. The leakage component of any of Clauses 2-8, wherein the fluid diversion member extends around a portion of a circumference of the first housing.

Clause 10. The leakage component of any of Clauses 2-9, wherein the fluid diversion member extends axially along an outer surface of the first housing.

Clause 11. The leakage component of Clause 10, wherein the fluid diversion member comprises a plurality of fluid diversion members forming fluid diversion channels therebetween.

Clause 12. The leakage component of any of Clauses 1-12, wherein a leakage port of the plurality of leakage ports comprises an elongate profile.

Clause 13. The leakage component of Clause 12, wherein the elongate profile comprises a port length greater than a port width.

Clause 14. The leakage component of Clause 13, wherein the port width ranges between about 0.5 mm and about 1 mm.

Clause 15. The leakage component of any of Clauses 12-14, wherein the leakage port comprises an aspect ratio between 3:1 to 9:1.

Clause 16. The leakage component of any of Clauses 12-15, wherein the leakage port of the plurality of leakage ports comprises a discorectangular profile.

Clause 17. The leakage component of any of Clauses 12-16, wherein the leakage port of the plurality of leakage ports extends along a flow axis.

Clause 18. The leakage component of any of Clauses 12-17, wherein the leakage port of the plurality of leakage ports extends circumferentially.

Clause 19. The leakage component of any of Clauses 1-18, wherein a leakage port of the plurality of leakage ports comprises a circular profile.

Clause 20. The leakage component of any of Clauses 1-19, wherein the plurality of leakage ports are disposed along a circumference of the first housing.

Clause 21. The leakage component of Clause 20, wherein the plurality of leakage ports are equidistantly angularly spaced along the circumference of the first housing.

Clause 22. The leakage component of Clauses 20 or 21, wherein the plurality of leakage ports are spaced apart between about 1.5 mm and about 2.5 mm.

Clause 23. The leakage component of any of Clauses 20-22, wherein the plurality of leakage ports are disposed within 180 degrees of the circumference of the first housing.

Clause 24. The leakage component of any of Clauses 20-23, wherein the plurality of leakage ports comprise a first set of leakage ports and a second set of leakage ports, the second set of leakage ports angularly spaced apart from the first set of leakage ports.

Clause 25. The leakage component of any of Clauses 1-24, wherein the plurality of leakage ports each comprise parallel port walls.

Clause 26. The leakage component of any of Clauses 1-24, wherein a first leakage port of the plurality of leakage ports is positioned adjacent to a second leakage port of the plurality of leakage ports, and wherein each of the plurality of leakage ports comprises a profile configured to entrain an exit flow from the adjacent leakage port.

Clause 27. The leakage component of Clause 26, further comprising a third leakage port of the plurality of leakage ports, wherein the second leakage port is positioned between the first and third leakage ports and the second leakage port is configured to direct fluid flow to entrain more of the exit flow from the first and second leakage ports than the ambient air.

Clause 28. The leakage component of Clause 27, wherein each leakage port of the plurality of leakage ports is formed by a first wall defining a length of the leakage port and a second wall defining a width of the leakage port, and wherein adjacent leakage ports are positioned with their respective first wall spaced apart and extending parallel relative to each other.

Clause 29. The leakage component of any of Clauses 1-28, further comprising: a second tubular housing defining a second flow path, wherein the second housing is coupled to the first housing to permit fluid communication between the first flow path and the second flow path.

Clause 30. The leakage component of Clause 29, wherein the second housing comprises at least one helical vane extending radially into the second flow path to induce rotation in the fluid flow in a second flow direction.

Clause 31. The leakage component of Clauses 29 or 30, wherein any of the first housing or the second housing comprises a ball joint surface defined along an outer surface thereof, and the other of the first housing or the second housing comprising a socket surface defined within an inner surface thereof, wherein the socket surface is configured to movably couple with the ball joint surface.

Clause 32. The leakage component of Clause 31, wherein a leakage port of the plurality of leakage ports is disposed proximal to the second end portion of the first housing.

Clause 33. The leakage component of Clauses 31 or 32, wherein the ball joint surface includes a shoulder extending radially from the outer surface and disposed opposite the second end portion, wherein a leakage port of the plurality of leakage ports is formed through the shoulder.

Clause 34. The leakage component of Clause 33, wherein the leakage port of the plurality of leakage ports extends circumferentially around the shoulder.

Clause 35. The leakage component of Clauses 33 or 34, wherein the leakage port of the plurality of leakage ports comprises a circular profile.

Clause 36. The leakage component of any of Clauses 31-35, wherein an edge of the socket surface comprises an axially undulating profile.

Clause 37. The leakage component of any of Clauses 31-36, wherein an edge of the socket surface comprises a scalloped profile.

Clause 38. The leakage component of any of Clauses 1-37, wherein the first housing comprises a cylindrical shape.

Clause 39. A leakage component, comprising: a tubular first housing defining a first flow path between a first end portion and a second end portion; a ball joint surface adjacent to the second end portion and defined along an outer surface of the first housing; a plurality of leakage ports formed in the first housing and in fluid communication with the first flow path, wherein fluid flow through the plurality of leakage ports is configured to entrain ambient air into the fluid flow exiting the plurality of leakage ports to decelerate the fluid flow; a tubular second housing defining a second flow path, wherein the second housing is coupled to the first housing to permit fluid communication between the first flow path and the second flow path; and a socket surface defined within an inner surface of the second housing, wherein the socket surface is configured to movably couple with the ball joint surface.

Clause 40. The leakage component of Clause 39, further comprising a fluid diversion member extending from the first housing and disposed adjacent to one or more leakage ports of the plurality of leakage ports, wherein the fluid diversion member is configured to divert fluid flow away from the one or more leakage ports in a first flow direction and to direct fluid flow toward the one or more leakage ports in a second flow direction.

Clause 41. The leakage component of Clauses 39 or 40, wherein a leakage port of the plurality of leakage ports comprises a discorectangular profile.

Clause 42. The leakage component of any of Clauses 39-41, wherein a leakage port of the plurality of leakage ports is disposed along the second end portion of the first housing.

Clause 43. A method to direct fluid flow, the method comprising: providing a tubular housing configured to accommodate a bulk inspiration flow and a bulk expiration flow; leaking the portion of the bulk expiration flow into environment via a plurality of leakage ports formed in the tubular housing, wherein each leakage port of the plurality of leakage ports comprises a fluid diversion member extending into the tubular housing and enshrouding a portion of the leakage port; diverting a portion of the bulk expiration flow away from the plurality of leakage ports via the fluid diversion member; and diverting a portion of the bulk expiration flow toward the plurality of leakage ports formed in the tubular housing via the fluid diversion member.

Clause 44. The method of Clause 44, further comprising swirling the portion of the bulk expiration flow within the housing.

Clause 45. The method of Clauses 43 or 44, wherein leaking the portion of the bulk expiration flow into environment comprises entraining ambient air into the portion of the bulk expiration flow to decelerate the portion of the bulk expiration flow.

Clause 46. The method of any of Clauses 43-45, further comprising: introducing a bulk inspiration flow to the housing; and directing the bulk inspiration flow from a ventilator end portion of the housing to a patient end portion of the housing.

Clause 47. The method of any of Clauses 43-46, further comprising: bending the housing at a ball joint; and directing the bulk expiration flow around a bend within the housing.

Clause 48. The method of Clause 47, further comprising controlling the portion of the bulk expiration flow to the plurality of leakage ports in response to bending the housing at the ball joint.

Clause 49. The method of any of Clauses 43-48, wherein a leakage port of the plurality of leakage ports comprises an elongate profile.

Clause 50. The method of Clause 49, wherein the elongate profile comprises a port length greater than a port width.

Clause 51. The method of Clause 50, wherein the port width ranges between about 0.5 mm and about 1 mm.

Clause 52. The method of any of Clauses 43-51, wherein a leakage port comprises an aspect ratio between 3:1 to 9:1.

Clause 53. The method of any of Clauses 43-52, wherein a leakage port of the plurality of leakage ports comprises a discorectangular profile.

Clause 54. The method of any of Clauses 43-53, wherein a leakage port of the plurality of leakage ports extends along a flow axis.

Clause 55. The method of any of Clauses 43-54, wherein a leakage port of the plurality of leakage ports extends circumferentially.

Clause 56. The method of any of Clauses 43-55, wherein a leakage port of the plurality of leakage ports comprises a circular profile.

Clause 57. The method of any of Clauses 43-56, wherein the plurality of leakage ports are disposed along a circumference of the housing.

Clause 58. The method of Clause 60, wherein the plurality of leakage ports are equidistantly angularly spaced along the circumference of the housing.

Clause 59. The method of any of Clauses 43-58, wherein the plurality of leakage ports are spaced apart between about 1.5 mm and about 2.5 mm.

Clause 60. The method of any of Clauses 43-59, wherein the plurality of leakage ports are disposed within 180 degrees of the circumference of the housing.

Clause 61. The method of any of Clauses 43-60, wherein the plurality of leakage ports comprise a first set of leakage ports and a second set of leakage ports, the second set of leakage ports angularly spaced apart from the first set of leakage ports.

Clause 62. The method of any of Clauses 43-61, wherein the plurality of leakage ports each comprise parallel port walls.

Clause 63. A leakage component, comprising: a tubular first housing defining a first flow path between a first end portion and a second end portion; a ball joint surface adjacent to the second end portion and defined along an outer surface of the first housing; a tubular second housing defining a second flow path, wherein the second housing is coupled to the first housing to permit fluid communication between the first flow path and the second flow path; a socket surface defined within an inner surface of the second housing, wherein the socket surface is configured to movably couple with the ball joint surface; and a leakage path defined between the second end portion of the first housing and the socket surface of the second housing, wherein the leakage path is in fluid communication with the first flow path.

Clause 64. The leakage component of Clause 63, wherein the ball joint surface defines a plurality of axial flow channels to direct the fluid flow from the leakage path away from the socket surface.

Clause 65. The leakage component of Clause 64, wherein the plurality of axial flow channels comprise a plurality of parallel channel walls.

Clause 66. The leakage component of Clause 65, wherein the plurality of channel walls each comprise an arcuate profile.

Clause 67. The leakage component of Clauses 65 or 66, wherein the ball joint surface defines a circumferential flow control rib to control the fluid flow from the leakage path.

Clause 68. A method to direct fluid flow, the method comprising: providing a tubular housing configured to accommodate a bulk expiration flow; diverting a portion of the bulk expiration flow to a plurality of leakage ports formed in the tubular housing; and entraining ambient air into the portion of the bulk expiration flow leaking through the plurality of leakage ports to reduce a velocity of the portion of the bulk expiration flow leaking through the plurality of leakage ports.

Clause 69. The method of Clause 68, further comprising entraining exit flow from an adjacent leakage port, wherein a first leakage port of the plurality of leakage ports is positioned adjacent to a second leakage port of the plurality of leakage ports.

Clause 70. The method of Clauses 68 or 69, wherein a third leakage port of the plurality of leakage ports, wherein the second leakage port is positioned between the first and third leakage ports; and further comprising entraining, by the fluid flow from the second leakage port, more of the exit flow from the first and second leakage ports than ambient air.

Clause 71. The method of Clause 70, wherein each leakage port of the plurality of leakage ports is formed by a first wall defining a length of the leakage port and a second wall defining a width of the leakage port, and wherein adjacent leakage ports are positioned with their respective first wall spaced apart and extending parallel relative to each other.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A leakage component, comprising:
  a tubular first housing defining a first flow path between a first end portion and a second end portion; and
  a plurality of leakage ports formed in the first housing and in fluid communication with the first flow path, wherein fluid flow through the plurality of leakage ports is configured to entrain ambient air into the fluid flow exiting the plurality of leakage ports to decelerate the fluid flow, a profile of each of the plurality of leakage ports comprises a discorectangular profile, the discorectangular profile comprising an elongated rectangular shape with semi-circular ends each having a diameter, and a leakage port of the plurality of leakage ports is separated from a neighboring leakage port of the plurality of leakage ports by a factor of the diameter of the semi-circular ends of the discorectangular profile.

2. The leakage component of claim 1, further comprising a fluid diversion member extending from the first housing and disposed adjacent to one or more leakage ports of the plurality of leakage ports, wherein the fluid diversion member is configured to divert fluid flow away from the one or more leakage ports in a first flow direction and to direct fluid flow toward the one or more leakage ports in a second flow direction.

3. The leakage component of claim 2, wherein the fluid diversion member extends radially into the first flow path and extends axially to enshroud the one or more leakage ports.

4. The leakage component of claim 3, wherein an outer surface of the fluid diversion member defines an inspiration flow path between the first end portion and the second end portion, and an inner surface of the fluid diversion member defines a partial expiration flow path between the second end portion and the one or more leakage ports.

5. The leakage component of claim 3, wherein the fluid diversion member enshrouds the plurality of leakage ports.

6. The leakage component of claim 3, wherein the fluid diversion member extends an axial length to at least partially axially overlap the one or more leakage ports.

7. The leakage component of claim 2, wherein the fluid diversion member extends around a portion of a circumference of the first housing.

8. The leakage component of claim 2, wherein the fluid diversion member extends axially along an outer surface of the first housing.

9. The leakage component of claim 1, wherein the plurality of leakage ports are disposed along a circumference of the first housing.

10. The leakage component of claim 1, wherein a profile of each of the leakage ports of the plurality of leakage ports each comprise parallel port walls.

11. The leakage component of claim 1, wherein a first leakage port of the plurality of leakage ports is positioned adjacent to a second leakage port of the plurality of leakage ports, and wherein the first leakage port and the second leakage port each comprises a profile configured to entrain an exit flow from the adjacent leakage port.

12. The leakage component of claim 1, further comprising:
  a tubular second housing defining a second flow path, wherein the second housing is coupled to the first housing to permit fluid communication between the first flow path and the second flow path.

13. The leakage component of claim 12, wherein any of the first housing or the second housing comprises a ball joint surface defined along an outer surface thereof, and the other of the first housing or the second housing comprising a socket surface defined within an inner surface thereof, wherein the socket surface is configured to movably couple with the ball joint surface.

14. The leakage component of claim 1, wherein the leakage port of the plurality of leakage ports is separated from the neighboring leakage port 1.9 mm or 2.9 times the diameter of the semi-circular ends of the discorectangular profile.

15. The leakage component of claim 1, wherein the leakage port of the plurality of leakage ports is separated from the neighboring leakage port approximately 0.5 mm, 1.0 mm, 1.5 mm, 2.0 mm, 2.5 mm, 3.0 mm, or 3.5 mm.

16. The leakage component of claim 1, wherein the semi-circular ends of the discorectangular profile each have a diameter equal to a width of the elongated rectangular shape.

17. A leakage component, comprising:
  a tubular first housing defining a first flow path between a first end portion and a second end portion;
  a ball joint surface adjacent to the second end portion and defined along an outer surface of the first housing;
  a plurality of leakage ports formed in the first housing and in fluid communication with the first flow path, wherein fluid flow through the plurality of leakage ports is configured to entrain ambient air into the fluid flow exiting the plurality of leakage ports to decelerate the fluid flow, a profile of each of the plurality of leakage ports comprises a discorectangular profile the discorectangular profile comprising an elongated rectangular shape with semi-circular ends each having a diameter, and a leakage port of the plurality of leakage ports is separated from a neighboring leakage port of the plurality of leakage ports by a factor of the diameter of the semi-circular ends of the discorectangular profile;
  a tubular second housing defining a second flow path, wherein the second housing is coupled to the first housing to permit fluid communication between the first flow path and the second flow path; and
  a socket surface defined within an inner surface of the second housing, wherein the socket surface is configured to movably couple with the ball joint surface.

18. The leakage component of claim 17, further comprising a fluid diversion member extending from the first housing and disposed adjacent to one or more leakage ports of the plurality of leakage ports, wherein the fluid diversion member is configured to divert fluid flow away from the one or more leakage ports in a first flow direction and to direct fluid flow toward the one or more leakage ports in a second flow direction.

19. A method to direct fluid flow, the method comprising:
providing a tubular housing configured to accommodate a bulk expiration flow;
diverting a portion of the bulk expiration flow to a plurality of leakage ports formed in the tubular housing, wherein a profile of each of the plurality of leakage ports comprises a discorectangular profile, the discorectangular profile comprising an elongated rectangular shape with semi-circular ends each having a diameter, and a leakage port of the plurality of leakage ports is separated from a neighboring leakage port of the plurality of leakage ports by a factor of the diameter of the semi-circular ends of the discorectangular profile; and
entraining ambient air into the portion of the bulk expiration flow leaking through the plurality of leakage ports to reduce a velocity of the portion of the bulk expiration flow leaking through the plurality of leakage ports.

20. The method of claim 19, further comprising entraining exit flow from an adjacent leakage port, wherein a first leakage port of the plurality of leakage ports is positioned adjacent to a second leakage port of the plurality of leakage ports.

\* \* \* \* \*